US011541111B2

(12) United States Patent
Pitcovski et al.

(10) Patent No.: US 11,541,111 B2
(45) Date of Patent: Jan. 3, 2023

(54) OPTIMIZED POLYPEPTIDE FOR A SUBUNIT VACCINE AGAINST AVIAN REOVIRUS

(71) Applicant: GAVISH-GALILEE BIO APPLICATIONS, LTD, Kiryat Shmona (IL)

(72) Inventors: Jacob Pitcovski, Korazim (IL); Dana Goldenberg, Lower Galilee (IL)

(73) Assignee: GAVISH-GALILEE BIO APPLICATIONS, LTD., Kiryat Shmona (IL)

( * ) Notice: Subject to any disclaimer, the term of this patent is extended or adjusted under 35 U.S.C. 154(b) by 0 days.

(21) Appl. No.: 16/068,548

(22) PCT Filed: Jan. 5, 2017

(86) PCT No.: PCT/IL2017/050011
§ 371 (c)(1),
(2) Date: Jul. 6, 2018

(87) PCT Pub. No.: WO2017/118977
PCT Pub. Date: Jul. 13, 2017

(65) Prior Publication Data
US 2019/0290752 A1    Sep. 26, 2019

Related U.S. Application Data

(60) Provisional application No. 62/275,838, filed on Jan. 7, 2016.

(51) Int. Cl.
*A61K 39/15* (2006.01)
*A61P 31/12* (2006.01)
*C07K 14/005* (2006.01)
*C12N 15/63* (2006.01)
*A61K 39/12* (2006.01)
*A61K 39/00* (2006.01)

(52) U.S. Cl.
CPC .............. *A61K 39/15* (2013.01); *A61K 39/12* (2013.01); *A61P 31/12* (2018.01); *C07K 14/005* (2013.01); *C12N 15/63* (2013.01); *A61K 2039/552* (2013.01); *C12N 2720/12022* (2013.01); *C12N 2720/12034* (2013.01)

(58) Field of Classification Search
None
See application file for complete search history.

(56) References Cited

U.S. PATENT DOCUMENTS 6,951,650 B1    10/2005    Van Loon
2007/0178115 A1*   8/2007    Tang ................. A61K 39/145
424/189.1

FOREIGN PATENT DOCUMENTS

| CN | 103642758 | 3/2014 |
| KR | 20140146803 A | 12/2014 |
| RU | 2 265 659 | 12/2005 |
| WO | 2008/076518 | 6/2008 |
| WO | 2009093251 A2 | 7/2009 |

OTHER PUBLICATIONS

GenBank Accession ACN56930, sigma C protein, partial [Avian orthoreovirus], 2010.*
GenBank Accession Q99212, RecName: Full=Sigma-C capsid protein; AltName: Full=Sigma-3 protein, 2015.*
GenBank Accession ACN56931, sigma C protein, partial [Avian orthoreovirus], 2010.*
Guardado-Calvo, Pablo, et al. Crystallographic structure of the alpha-helical triple coiled-coil domain of avian reovirus S1133 fibre. Journal of General Virology, 90.3: pp. 672-677.2009.
Van Raaij, Mark J., et al. Crystallization of the C-terminal globular domain of avian reovirus fibre. Acta Crystallographica Section F: Structural Biology and Crystallization Communications, pp. 651-654. 2005.
Lin, Kuan-Hsun, et al. Avian reovirus sigma C enhances the mucosal and systemic immune responses elicited by antigen-conjugated lactic acid bacteria. Vaccine, 2012, 30(3), pp. 5019-5029. Abstract Only.
Wu, H., et al. Yeast-derived sigma C protein-induced immunity against avian reovirus. Avian Diseases, 2005, 49.2: 281-284.
Goldenberg, Dana, et al. Optimized polypeptide for a subunit vaccine against avian reovirus. Vaccine, 2016, 34.27: 3178-3183.
Benavente, J. & Martfnez-Costas, J., 2007. Avian reovirus: Structure and biology. Virus Research, 123(2), pp. 105-119.
Fingerut, E. et al., 2003. A subunit vaccine against the adenovirus egg-drop syndrome using part of its fiber protein. Vaccine, 21, pp. 2761-2766.
Goldenberg, D. et al., 2010. Genetic and antigenic characterization of sigma C protein from avian reovirus. Avian Pathology 39(3), pp. 189-199.

(Continued)

*Primary Examiner* — Benjamin P Blumel
(74) *Attorney, Agent, or Firm* — Wenderoth, Lind & Ponack, L.L.P.

(57) ABSTRACT

An isolated polypeptide comprising an amino acid sequence corresponding to the amino acid residues forming a full or partial α-helical domain, the hinge domain, the β-triple spiral domain and a full or partial globular head domain of an avian reovirus sigma C protein, and lacking the amino acid sequence that is N-terminal to said α-helical domain is provided. Furthermore, a vaccine comprising, or a viral vector expressing, at least one of the isolated polypeptides of the present invention is provided.

23 Claims, 4 Drawing Sheets

Specification includes a Sequence Listing.

(56) References Cited

OTHER PUBLICATIONS

Martinez-Costas, J. et al., 1997. Protein Architecture of Avian Reovirus S1133 and Identification of the Cell Attachment Protein. J. Virology 71(1), pp. 59-64.

Guardado Calvo, P. et al., 2005. Structure of the Carboxy-terminal Receptor-binding Domain of Avian Reovirus Fibre SigmaC. Journal of Molecular Biology, 354(1), pp. 137-149.

Van der Heide, L., Kalbac, M. & Brustolon, M., 1983. Development of an attenuated apathogenic reovirus vaccine against viral arthritis/tenosynovitis. Avian Diseases, 27(3), pp. 698-706.

Jones, R.C., 2000. Avian reovirus infections. Revue scientifique et technique (International Office of Epizootics), 19(2), pp. 614-625.

Jung, K.M. et al., 2014. Use of IgY antibody to recombinant avian reovirus σC protein in the virus diagnostics. Acta virologica, 58(2), pp. 108-113.

Kant, A. et al., 2003. Classification of Dutch and German avian reoviruses by sequencing the sigma C protein. Veterinary Research, 34(2), pp. 203-212.

Lublin, A. et al., 2011. Wide-range protection against avian reovirus conferred by vaccination with representatives of four defined genotypes. Vaccine, 29(47), pp. 8683-8688.

McAleer, W.J. et al., 1984. Human hepatitis B vaccine from recombinant yeast. Nature, 307(5947), pp. 178-180.

Pitcovski, J. et al., 2005. A subunit vaccine against hemorrhagic enteritis adenovirus. Vaccine, 23, pp. 4697-4702.

Pitcovski, J. et al., 2003. Development and large-scale use of recombinant VP2 vaccine for the prevention of infectious bursal disease of chickens. Vaccine, 21, pp. 4736-4743.

Shapouri, M.R. et al., 1995. Cloning, sequencing and expression of the S1 gene of avian reovirus. The Journal of General Virology, 76, pp. 1515-1520.

Shapouri, M.R.S. et al., 1996. Characterization of monoclonal antibodies against avian reovirus strain S1133. Avian Pathology 25(1), pp. 57-67.

Troxler, S. et al., 2013. Identification of a new reovirus causing substantial losses in broiler production in France, despite routine vaccination of breeders. Veterinary Record, 172(21), p. 556-562.

Vasserman, Y. et al., 2004. The influence of reovirus sigma C protein diversity on vaccination efficiency. Avian Diseases, 48(2), pp. 271-278.

Valentino, K. & Poronsky, C.B., 2016. Human Papillomavirus Infection and Vaccination. Journal of Pediatric Nursing 31, pp. e155-e166.

Protein data base: Accession No. 2VRS_A. Chain A, Structure of Avian Reovirus Sigma C 117-326, C2 Crystal Form. Feb. 20, 2018.

International Search Report and Written Opinion, dated May 11, 2017 in counterpart international application No. PCT/IL2017/050011.

Chen, Shi-long et al., "Preparation and the Efficacy Evaluation of an Oil-emulsion Inactivated Vaccine Against Novel Duck Reovirus Disease", Fujian Journal of Agricultural Sciences, 2012, vol. 27, No. 5, pp. 461-464, English-language abstract.

* cited by examiner

SEQUENCE LISTING

```
<160> NUMBER OF SEQ ID NOS: 34

<210> SEQ ID NO 1
<211> LENGTH: 326
<212> TYPE: PRT
<213> ORGANISM: Avian reovirus

<400> SEQUENCE: 1

Met Ala Gly Leu Asn Pro Ser Gln Arg Arg Glu Val Val Ser Leu Ile
1               5                   10                  15

Leu Ser Leu Thr Ser Asn Val Asn Ile Ser His Gly Asp Leu Thr Pro
            20                  25                  30

Ile Tyr Glu Arg Leu Thr Asn Leu Glu Ala Ser Thr Glu Leu Leu His
        35                  40                  45

Arg Ser Ile Ser Asp Ile Ser Thr Thr Val Ser Asn Ile Ser Ala Asn
    50                  55                  60

Leu Gln Asp Met Thr His Thr Leu Asp Asp Val Thr Ala Asn Leu Asp
65                  70                  75                  80

Gly Leu Arg Thr Thr Val Thr Ala Leu Gln Asp Ser Val Ser Ile Leu
                85                  90                  95

Ser Thr Asn Val Thr Asp Leu Thr Asn Arg Ser Ser Ala His Ala Ala
            100                 105                 110

Ile Leu Ser Ser Leu Gln Thr Thr Val Asp Gly Asn Ser Thr Ala Ile
        115                 120                 125
```

```
Ser Asn Leu Lys Ser Asp Ile Ser Ser Asn Gly Leu Ala Ile Thr Asp
    130                 135                 140
Leu Gln Asp Arg Val Lys Ser Leu Glu Ser Thr Ala Ser His Gly Leu
145                 150                 155                 160
Ser Phe Ser Pro Pro Leu Ser Val Ala Asp Gly Val Val Ser Leu Asp
                165                 170                 175
Met Asp Pro Tyr Phe Cys Ser Gln Arg Val Ser Leu Thr Ser Tyr Ser
            180                 185                 190
Ala Glu Ala Gln Leu Met Gln Phe Arg Trp Met Ala Arg Gly Thr Asn
        195                 200                 205
Gly Ser Ser Asp Thr Ile Asp Met Thr Val Asn Ala His Cys His Gly
    210                 215                 220
Arg Arg Thr Asp Tyr Met Met Ser Ser Thr Gly Asn Leu Thr Val Thr
225                 230                 235                 240
Ser Asn Val Val Leu Leu Thr Phe Asp Leu Ser Asp Ile Thr His Ile
                245                 250                 255
Pro Ser Asp Leu Ala Arg Leu Val Pro Ser Ala Gly Phe Gln Ala Ala
            260                 265                 270
Ser Phe Pro Val Asp Val Ser Phe Thr Arg Asp Ser Ala Thr His Ala
        275                 280                 285
Tyr Gln Ala Tyr Gly Val Tyr Ser Ser Arg Val Phe Thr Ile Thr
    290                 295                 300
Phe Pro Thr Gly Gly Asp Gly Thr Ala Asn Ile Arg Ser Leu Thr Val
305                 310                 315                 320
Arg Thr Gly Ile Asp Thr
                325
```

<210> SEQ ID NO 2
<211> LENGTH: 205
<212> TYPE: PRT
<213> ORGANISM: Artificial Sequence
<220> FEATURE:
<223> OTHER INFORMATION: synthetic

<400> SEQUENCE: 2

```
Asp Gly Asn Ser Thr Ala Ile Ser Asn Leu Lys Ser Asp Ile Ser Ser
1               5                   10                  15
Asn Gly Leu Ala Ile Thr Asp Leu Gln Asp Arg Val Lys Ser Leu Glu
                20                  25                  30
Ser Thr Ala Ser His Gly Leu Ser Phe Ser Pro Pro Leu Ser Val Ala
            35                  40                  45
Asp Gly Val Val Ser Leu Asp Met Asp Pro Tyr Phe Cys Ser Gln Arg
        50                  55                  60
Val Ser Leu Thr Ser Tyr Ser Ala Glu Ala Gln Leu Met Gln Phe Arg
65                  70                  75                  80
Trp Met Ala Arg Gly Thr Asn Gly Ser Ser Asp Thr Ile Asp Met Thr
                85                  90                  95
Val Asn Ala His Cys His Gly Arg Arg Thr Asp Tyr Met Met Ser Ser
            100                 105                 110
Thr Gly Asn Leu Thr Val Thr Ser Asn Val Val Leu Leu Thr Phe Asp
        115                 120                 125
Leu Ser Asp Ile Thr His Ile Pro Ser Asp Leu Ala Arg Leu Val Pro
    130                 135                 140
Ser Ala Gly Phe Gln Ala Ala Ser Phe Pro Val Asp Val Ser Phe Thr
145                 150                 155                 160
```

```
Arg Asp Ser Ala Thr His Ala Tyr Gln Ala Tyr Gly Val Tyr Ser Ser
            165                 170                 175

Ser Arg Val Phe Thr Ile Thr Phe Pro Thr Gly Gly Asp Gly Thr Ala
            180                 185                 190

Asn Ile Arg Ser Leu Thr Val Arg Thr Gly Ile Asp Thr
            195                 200                 205

<210> SEQ ID NO 3
<211> LENGTH: 205
<212> TYPE: PRT
<213> ORGANISM: Artificial Sequence
<220> FEATURE:
<223> OTHER INFORMATION: synthetic

<400> SEQUENCE: 3

Gln Ala Leu Leu Val Glu Val Ser Asn Leu Lys Ser Ser Val Ser Ser
1               5                   10                  15

Gln Gly Leu Thr Ile Ser Asn Leu Glu Arg Arg Val Gln Ala Leu Glu
            20                  25                  30

Gly Gly Ser Ser Thr Thr Leu Ser Phe Ala Asp Pro Leu Lys Leu Glu
            35                  40                  45

Asp Gly Thr Val Ser Leu Glu Leu Asp Pro Tyr Phe Cys Ser Val Ser
        50                  55                  60

Arg Asn Leu Thr Ser Tyr Ser Ala Gly Ala Gln Leu Met Gln Phe Gln
65                  70                  75                  80

Trp Ser Val Lys Gly Glu Asp Gly Ala Ala Asn Ser Ile Asp Met Asp
                85                  90                  95

Val Asn Ala His Ser His Gly Pro Arg Thr Asp Tyr Leu Met Ser Thr
            100                 105                 110

Lys Gln Ser Leu Thr Val Thr Thr Ser Pro Ala Thr Leu Val Phe Glu
            115                 120                 125

Leu Asp Arg Ile Thr Ser Leu Pro Ser Asp Leu Ser Arg Leu Ile Pro
        130                 135                 140

Cys His Gly Phe Gln Gln Ala Thr Phe Pro Val Asp Ile Ser Phe Gln
145                 150                 155                 160

Arg Asp Gly Val Ser His Thr Tyr Gln Val Tyr Gly Lys Tyr Ser Ser
                165                 170                 175

Ser Arg Val Phe Thr Ile Thr Phe Pro Thr Gly Gly Asp Gly Thr Ala
            180                 185                 190

Asn Ile Arg Ser Leu Thr Val Arg Thr Gly Ile Asp Thr
            195                 200                 205

<210> SEQ ID NO 4
<211> LENGTH: 205
<212> TYPE: PRT
<213> ORGANISM: Artificial Sequence
<220> FEATURE:
<223> OTHER INFORMATION: synthetic

<400> SEQUENCE: 4

Asn Gly Asn Ser Ser Ala Ile Ser Asn Leu Arg Asn Asp Val Ser Ala
1               5                   10                  15

Ser Gly Leu Asn Ile Thr Asp Leu Gln Asn Arg Val Lys Ser Leu Glu
            20                  25                  30

Ser Asp Thr Ser His Gly Leu Ser Phe Ser Pro Pro Leu Ser Val Ala
        35                  40                  45

Asp Gly Val Val Ser Leu Asp Met Asp Pro Tyr Phe Cys Ser Gln Arg
        50                  55                  60
```

Val Ser Leu Thr Ser Tyr Ser Ala Glu Ala Arg Leu Met Gln Phe Gln
65                  70                  75                  80

Trp Val Ala Lys Gly Thr Ser Gly Ser Ser Asp Thr Ile Asp Met Thr
                85                  90                  95

Val Asn Ala His Cys His Gly Arg Arg Thr Asp Tyr Met Met Ser Ser
            100                 105                 110

Thr Gly Gly Leu Thr Val Thr Ser Asn Ala Val Ser Leu Thr Phe Asp
            115                 120                 125

Leu Ser Tyr Ile Thr Asn Met Pro Ser Asp Leu Ser Arg Leu Ile Pro
            130                 135                 140

Ser Ala Gly Phe Gln Val Ala Ser Phe Pro Val Asp Val Ser Phe Thr
145                 150                 155                 160

Arg Glu Ser Ser Thr His Thr Tyr Gln Val Tyr Gly Ala Tyr Ser Ser
                165                 170                 175

Ala Arg Val Phe Thr Ile Thr Phe Pro Thr Gly Gly Asn Gly Thr Ser
            180                 185                 190

Asn Ile Arg Phe Leu Thr Val Arg Thr Gly Ile Asp Thr
            195                 200                 205

<210> SEQ ID NO 5
<211> LENGTH: 205
<212> TYPE: PRT
<213> ORGANISM: Artificial Sequence
<220> FEATURE:
<223> OTHER INFORMATION: synthetic

<400> SEQUENCE: 5

Asn Ala Asn Val Thr Asp Ile Ala Asn Leu Lys Gly Ser Val Thr Thr
1               5                   10                  15

Leu Ser Leu Thr Val Thr Asp Leu Glu Lys Arg Leu Lys Val Val Glu
                20                  25                  30

Ser Gly Ser Ser Ser Ser Leu Glu Phe Thr Ser Pro Leu Ser Leu Thr
            35                  40                  45

Asp Gly Val Val Ser Leu Asn Met Asp Pro Tyr Phe Cys Ser Asp Asn
50                  55                  60

His Ala Leu Thr Ser Tyr Ser Ser Asp Ala Gln Leu Met Gln Phe Gln
65                  70                  75                  80

Trp Leu Ala Arg Gly Asp Asp Gly Ser Ala Gly Ser Val Glu Met Leu
                85                  90                  95

Val Asn Ala His Cys His Gly Arg Arg Thr Asp Tyr Met Met Ser Thr
            100                 105                 110

Thr Glu Asn Leu Thr Val Thr Gly Asn Ser Thr Ser Leu Val Phe Ser
            115                 120                 125

Leu Asp Tyr Ile Thr Lys Pro Pro Ser Asp Met Ser Arg Leu Val Pro
            130                 135                 140

Arg Ala Gly Phe Gln Ala Ala Ser Phe Pro Val Asp Val Ser Phe Thr
145                 150                 155                 160

Arg Asp Thr Thr Thr His Ala Tyr Gln Val Tyr Gly Ala Tyr Ser Ser
                165                 170                 175

Ser Arg Val Phe Thr Ile Thr Phe Pro Thr Gly Gly Asp Gly Thr Ala
            180                 185                 190

Asn Ile Arg Ser Leu Thr Val Arg Thr Gly Ile Asp Thr
            195                 200                 205

<210> SEQ ID NO 6

<211> LENGTH: 267
<212> TYPE: PRT
<213> ORGANISM: Avian reovirus

<400> SEQUENCE: 6

Gly Asp Leu Lys Ser Val Tyr Glu Arg Leu Thr Ser Leu Glu Ala Ser
1               5                   10                  15

Thr Glu Ser Leu Arg Gln Ser Val Ser Gly Met Ser Val Thr Leu Ser
            20                  25                  30

Asp Leu Ser Ala Asp Leu Gln Asp Thr Thr Arg Ala Leu Asp Asp Val
        35                  40                  45

Thr Val Thr Leu Asn Asn Leu Ser Ala Thr Ile Thr Ala Leu Gln Ser
    50                  55                  60

Ser Val Thr Thr Leu Ser Ala Thr Val Asp Glu Leu Thr Asn Thr Ser
65                  70                  75                  80

Ser Ala His Ser Gly Met Leu Ser Ser Leu Gln Thr Ile Ile Asn Gly
                85                  90                  95

Asn Ser Ser Ala Ile Ser Asn Leu Arg Asn Asp Val Ser Ala Ser Gly
            100                 105                 110

Leu Asn Ile Thr Asp Leu Gln Asn Arg Val Lys Ser Leu Glu Ser Asp
        115                 120                 125

Thr Ser His Gly Leu Ser Phe Ser Pro Pro Leu Ser Val Ala Asp Gly
    130                 135                 140

Val Val Ser Leu Asp Met Asp Pro Tyr Phe Cys Ser Gln Arg Val Ser
145                 150                 155                 160

Leu Thr Ser Tyr Ser Ala Glu Ala Arg Leu Met Gln Phe Gln Trp Val
                165                 170                 175

Ala Lys Gly Thr Ser Gly Ser Ser Asp Thr Ile Gly Met Thr Val Asn
            180                 185                 190

Ala His Cys His Gly Arg Arg Thr Asp Tyr Met Met Ser Ser Thr Gly
        195                 200                 205

Gly Leu Thr Val Thr Ser Asn Ala Val Ser Leu Thr Phe Asp Leu Ser
    210                 215                 220

Tyr Ile Thr Asn Met Pro Ser Asp Leu Ser Arg Leu Ile Pro Ser Ala
225                 230                 235                 240

Gly Phe Gln Val Ala Ser Phe Pro Val Asp Val Ser Phe Thr Arg Glu
                245                 250                 255

Ser Ser Thr His Thr Tyr Gln Val Tyr Gly Ala
            260                 265

<210> SEQ ID NO 7
<211> LENGTH: 268
<212> TYPE: PRT
<213> ORGANISM: Avian reovirus

<400> SEQUENCE: 7

Gly Asp Leu Lys Ser Val Tyr Glu Arg Leu Asn

Ser Ala His Ser Gly Met Leu Ser Ser Leu Gln Thr Ile Ile Asn Gly
             85                  90                  95

Asn Ser Ser Ala Ile Ser Asn Leu Arg Asn Asp Val Ser Ala Ser Gly
            100                 105                 110

Phe Asp Ile Ser Asp Leu Gln Asn Arg Val Lys Ser Leu Glu Ser Asp
        115                 120                 125

Thr Ser His Gly Leu Ser Phe Ser Pro Leu Ser Val Ala Asp Gly
    130                 135                 140

Val Val Ser Leu Asp Met Asp Pro Tyr Phe Cys Ser Gln Arg Val Ser
145                 150                 155                 160

Leu Thr Ser Tyr Ser Ala Glu Ala Arg Leu Met Gln Phe Gln Trp Val
                165                 170                 175

Ala Lys Gly Thr Ser Gly Ser Ser Asp Thr Ile Asp Met Thr Val Asn
            180                 185                 190

Ala His Cys His Gly Arg Arg Thr Asp Tyr Met Met Ser Ser Thr Gly
        195                 200                 205

Gly Leu Thr Val Thr Ser Asn Ala Val Ser Leu Thr Phe Asp Leu Ser
    210                 215                 220

Tyr Ile Thr Asn Met Pro Ser Asp Leu Ser Arg Leu Ile Pro Ser Ala
225                 230                 235                 240

Gly Phe Gln Val Ala Ser Phe Pro Val Asp Val Ser Phe Thr Arg Glu
                245                 250                 255

Ser Ser Thr His Thr Tyr Gln Val Tyr Gly Ala Tyr
            260                 265

<210> SEQ ID NO 8
<211> LENGTH: 315
<212> TYPE: PRT
<213> ORGANISM: Avian reovirus

<400> SEQUENCE: 8

Ser Ser Gln Arg Arg Glu Val Val Ser Leu Ile Leu Ser Leu Asn Ser
1               5                   10                  15

Asn Val Thr Ile Asn Pro Gly Asp Leu Lys Ser Val Tyr Glu Arg Leu
            20                  25                  30

Asn Ser Leu Glu Ala Ser Thr Glu Ser Leu Arg Gln Ser Val Ser Gly
        35                  40                  45

Met Ser Val Thr Leu Ser Asp Leu Ser Ala Asp Leu Gln Asp Thr Thr
    50                  55                  60

Arg Ala Leu Asp Asp Val Thr Val Thr Leu Asn Asn Leu Ser Ala Thr
65                  70                  75                  80

Ile Thr Ala Leu Gln Ser Ser Val Thr Thr Leu Ser Ala Thr Val Asp
                85                  90                  95

Glu Leu Thr Asn Thr Ser Ser Ala His Ser Gly Met Leu Ser Ser Leu
            100                 105                 110

Gln Thr Ile Ile Asn Gly Asn Ser Ser Ala Ile Ser Asn Leu Arg Asn
        115                 120                 125

Asp Val Ser Ala Ser Gly Leu Asn Ile Thr Asp Leu Gln Asn Arg Val
    130                 135                 140

Lys Ser Leu Glu Ser Asp Thr Ser His Gly Leu Ser Phe Ser Pro Pro
145                 150                 155                 160

Leu Ser Val Ala Asp Gly Val Val Ser Leu Asp Met Asp Pro Tyr Phe
                165                 170                 175

Cys Ser Gln Arg Val Ser Leu Thr Ser Tyr Ser Ala Glu Ala Arg Leu

-continued

```
            180                 185                 190

Met Gln Phe Gln Trp Val Ala Lys Gly Thr Ser Gly Ser Ser Asp Thr
        195                 200                 205

Ile Asp Met Thr Val Asn Ala His Cys His Gly Arg Arg Thr Asp Tyr
    210                 215                 220

Met Met Ser Ser Thr Gly Gly Leu Thr Val Thr Ser Asn Ala Val Ser
225                 230                 235                 240

Leu Thr Phe Asp Leu Ser Tyr Ile Thr Asn Met Pro Ser Asp Leu Ser
                245                 250                 255

Arg Leu Ile Pro Ser Ala Gly Phe Gln Val Ala Ser Phe Pro Val Asp
            260                 265                 270

Val Ser Phe Thr Arg Glu Ser Ser Thr His Thr Tyr Gln Val Tyr Gly
        275                 280                 285

Ala Tyr Ser Ser Ala Arg Val Phe Thr Ile Thr Phe Pro Thr Gly Gly
    290                 295                 300

Asn Gly Thr Ser Asn Ile Arg Phe Leu Thr Val
305                 310                 315

<210> SEQ ID NO 9
<211> LENGTH: 301
<212> TYPE: PRT
<213> ORGANISM: Avian reovirus

<400> SEQUENCE: 9

Gln Arg Arg Glu Val Val Ser Leu Ile Leu Ser Leu Thr Ser Asn Ala
1               5                   10                  15

Thr Ile Asn Pro Gly Asp Leu Thr Ser Ile Arg Glu Arg Leu Thr Ser
            20                  25                  30

Leu Glu Ala Ser Thr Glu Ser Leu Ser Arg Ser Ile Ser Ser Met Ser
        35                  40                  45

Thr Thr Val Ser Asp Leu Ser Ala Asp Leu Gln Asn Val Thr Arg Ala
    50                  55                  60

Leu Asp Asp Val Thr Ala Asn Leu Asn Gly Ile Arg Val Thr Ile Thr
65                  70                  75                  80

Thr Leu Gln Asp Ser Val Ser Thr Leu Ser Thr Thr Val Thr Asp Leu
                85                  90                  95

Ser Arg Thr Ser Ser Ala His Ser Glu Ala Leu Ser Ser Leu Arg Thr
            100                 105                 110

Ile Val Asp Gly Asn Ser Thr Ile Ile Gly Asn Leu Lys Ser Asp Val
        115                 120                 125

Ala Ser Asn Gly Leu Ala Ile Thr Asp Leu Gln Ser Arg Val Lys Ser
    130                 135                 140

Leu Glu Ser Ala Ser Ser His Gly Leu Ser Phe Ser Pro Pro Leu Ser
145                 150                 155                 160

Val Ala Asp Gly Val Val Ser Leu Asn Leu Asp Pro Tyr Phe Cys Ser
                165                 170                 175

Gln Arg Val Ser Leu Thr Ser Tyr Ser Ala Glu Ala Leu Leu Met Gln
            180                 185                 190

Phe Gln Trp Met Ala Arg Gly Thr Asn Gly Ser Ala Asp Asn Ile Asp
        195                 200                 205

Met Thr Val Asn Ala His Cys His Gly Arg Arg Thr Asp Tyr Ile Met
    210                 215                 220

Ser Ser Thr Gly Gly Leu Thr Val Thr Gln Asn Ala Val Ser Leu Thr
225                 230                 235                 240
```

```
Phe Asp Leu Ser Tyr Ile Thr Arg Phe Pro Ser Asp Leu Ser Arg Leu
            245                 250                 255

Ile Pro Ser Ala Gly Phe Gln Ala Ala Ser Phe Pro Val Asp Val Ser
        260                 265                 270

Phe Thr Arg Gly Ser Thr Thr His Thr Tyr Gln Ala Tyr Gly Val Tyr
        275                 280                 285

Ser Ser Ser Arg Ile Phe Thr Ile Thr Phe Pro Thr Gly
        290                 295                 300

<210> SEQ ID NO 10
<211> LENGTH: 316
<212> TYPE: PRT
<213> ORGANISM: Avian reovirus

<400> SEQUENCE: 10

Gln Arg Arg Glu Val Val Ser Leu Ile Leu Ser Leu Asn Ser Asn Val
1               5                   10                  15

Thr Ile Asn Pro Gly Asp Leu Lys Ser Val Tyr Glu Arg Leu Thr Ser
            20                  25                  30

Leu Glu Ala Ser Thr Glu Ser Leu Arg Gln Ser Val Ser Gly Met Ser
        35                  40                  45

Val Thr Leu Ser Asp Leu Ser Ala Asp Leu Gln Asp Thr Thr Arg Ala
    50                  55                  60

Leu Asp Asp Val Thr Val Thr Leu Asn Asn Leu Ser Ala Thr Ile Thr
65                  70                  75                  80

Ala Leu Gln Ser Ser Val Thr Thr Leu Ser Ala Thr Val Asp Glu Leu
                85                  90                  95

Thr Asn Thr Ser Ser Ala His Ser Gly Met Leu Ser Ser Leu Gln Thr
            100                 105                 110

Ile Ile Asn Gly Asn Ser Ser Ala Ile Ser Asn Leu Arg Asn Asp Val
        115                 120                 125

Ser Ala Ser Gly Leu Asn Ile Thr Asp Leu Gln Asn Arg Val Lys Ser
    130                 135                 140

Leu Glu Ser Asp Thr Ser His Gly Leu Ser Phe Ser Pro Pro Leu Ser
145                 150                 155                 160

Val Ala Asp Gly Val Val Ser Leu Asp Met Asp Pro Tyr Phe Cys Ser
                165                 170                 175

Gln Arg Val Ser Leu Thr Ser Tyr Ser Ala Glu Ala Arg Leu Met Gln
            180                 185                 190

Phe Gln Trp Val Ala Lys Gly Thr Ser Gly Ser Ser Asp Thr Ile Asp
        195                 200                 205

Met Thr Val Asn Ala His Cys His Gly Arg Arg Thr Asp Tyr Met Met
    210                 215                 220

Ser Ser Thr Gly Gly Leu Thr Val Thr Ser Asn Ala Val Ser Leu Thr
225                 230                 235                 240

Phe Asp Leu Ser Tyr Ile Thr Asn Met Pro Ser Asp Leu Ser Arg Leu
                245                 250                 255

Ile Pro Ser Ala Gly Phe Gln Val Ala Ser Phe Pro Val Asp Val Ser
            260                 265                 270

Phe Thr Arg Glu Ser Ser Thr His Thr Tyr Gln Val Tyr Gly Ala Tyr
        275                 280                 285

Ser Ser Ala Arg Val Phe Thr Ile Thr Phe Pro Thr Gly Gly Asn Gly
    290                 295                 300

Thr Ser Asn Ile Arg Phe Leu Thr Leu Arg Thr Gly
305                 310                 315
```

<210> SEQ ID NO 11
<211> LENGTH: 318
<212> TYPE: PRT
<213> ORGANISM: Avian reovirus

<400> SEQUENCE: 11

```
Ser Gln Arg Arg Glu Val Val Ser Leu Ile Leu Ser Leu Thr Ser Asn
1               5                   10                  15

Ala Thr Ile Asn Pro Gly Asp Leu Thr Ser Ile Arg Glu Arg Leu Thr
            20                  25                  30

Ser Leu Glu Ala Ser Thr Glu Ser Leu Ser Arg Ser Ile Ser Ser Met
        35                  40                  45

Ser Thr Thr Val Ser Asp Leu Ser Ala Asp Leu Gln Asn Val Thr Arg
    50                  55                  60

Ala Leu Asp Asp Val Thr Ala Asn Leu Asn Gly Ile Arg Val Thr Ile
65                  70                  75                  80

Thr Thr Leu Gln Asp Ser Val Ser Thr Leu Ser Thr Thr Val Thr Asp
                85                  90                  95

Leu Ser Arg Thr Ser Ser Ala His Ser Glu Ser Leu Ser Ser Leu Arg
            100                 105                 110

Thr Ile Val Asp Gly Asn Ser Thr Ile Ile Gly Asn Leu Lys Ser Asp
        115                 120                 125

Val Ala Ser Asn Gly Leu Ala Ile Thr Asp Leu Gln Ser Arg Val Lys
    130                 135                 140

Pro Leu Glu Ser Ala Ser Ser His Gly Leu Ser Phe Ser Pro Pro Leu
145                 150                 155                 160

Ser Val Ala Asp Gly Val Val Ser Leu Asn Leu Asp Pro Tyr Phe Cys
                165                 170                 175

Ser Gln Arg Val Ser Leu Ala Ser Tyr Ser Ala Glu Ala Leu Leu Met
            180                 185                 190

Gln Phe Gln Trp Met Ala Arg Gly Thr Asn Gly Ser Ala Asp Asn Ile
        195                 200                 205

Asp Met Thr Val Asn Ala His Cys His Gly Arg Arg Thr Asp Tyr Ile
    210                 215                 220

Met Ser Ser Thr Gly Gly Leu Thr Val Thr Gln Asn Ala Val Ser Leu
225                 230                 235                 240

Thr Phe Asp Leu Ser Tyr Ile Thr Arg Phe Pro Ser Asp Leu Ser Arg
                245                 250                 255

Leu Ile Pro Ser Ala Gly Phe Gln Ala Ala Ser Phe Pro Val Asp Val
            260                 265                 270

Ser Phe Thr Arg Gly Ser Thr Thr His Thr Tyr Gln Ala Tyr Gly Val
        275                 280                 285

Tyr Ser Ser Ser Arg Ile Phe Thr Ile Thr Phe Pro Thr Gly Gly Asp
    290                 295                 300

Gly Pro Ala Asn Ile Arg Phe Leu Thr Val Arg Thr Gly Ile
305                 310                 315
```

<210> SEQ ID NO 12
<211> LENGTH: 267
<212> TYPE: PRT
<213> ORGANISM: Avian reovirus

<400> SEQUENCE: 12

```
Gly Asp Leu Met Gln Ile His Glu Arg Leu Ser Ala Leu Glu Leu Thr
1               5                   10                  15
```

```
Thr Thr Ser Leu Asn Asp Ser Val Asn Thr Ala Leu Ser Lys Val Thr
        20                  25                  30

Asp Leu Ser Gly Ser Leu Asp Asn Met Ala Val Ser Leu Ala Glu Thr
        35                  40                  45

Glu Gly Glu Leu Ile Lys Leu Ser Ser Ala Val Gln Cys Leu Arg Thr
 50                  55                  60

Ser Leu Asp His Leu Leu Gln Asn Trp Arg Leu Cys Pro His Trp Tyr
 65                  70                  75                  80

Val Thr His Gly Ser Ser Ile Ser Asp Leu Gln Lys Glu Gly Gln Ala
                85                  90                  95

Leu Ser Ser Glu Val Asn Asn Leu Asn Leu His Val Ser Ser Gln Gly
                100                 105                 110

Leu Thr Val Ser Asn Leu Glu Arg Arg Val Gln Ala Leu Glu Gly Gly
                115                 120                 125

Ser Ser Thr Thr Leu Ser Phe Ala Asp Pro Leu Lys Phe Glu Asp Gly
130                 135                 140

Thr Val Ser Leu Glu Leu Asp Pro Tyr Phe Cys Ser Val Ser Arg Asn
145                 150                 155                 160

Leu Thr Ser Tyr Ser Ala Gly Ala Gln Leu Met Gln Phe Gln Trp Ser
                165                 170                 175

Val Lys Gly Glu Asp Gly Ala Ala Asn Ser Ile Asp Met Asp Val Asn
                180                 185                 190

Ala His Ser His Gly Pro Arg Thr Asp Tyr Leu Met Ser Thr Lys Gln
                195                 200                 205

Ser Leu Thr Val Thr Ser Leu Leu Ala Thr Leu Val Phe Glu Leu Gly
                210                 215                 220

Arg Ile Thr Ser Leu Pro Ser Asp Leu Ser Arg Leu Ile Pro Cys His
225                 230                 235                 240

Gly Phe Gln Gln Ala Thr Phe Pro Val Asp Ile Ser Phe Gln Arg Asp
                245                 250                 255

Gly Val Ser His Thr Tyr Gln Val Tyr Gly Lys
                260                 265

<210> SEQ ID NO 13
<211> LENGTH: 305
<212> TYPE: PRT
<213> ORGANISM: Avian reovirus

<400> SEQUENCE: 13

Leu Ile Leu Ser Leu Thr Ser Ser Val Thr Ile Ser Pro Gly Asp Leu
 1               5                  10                  15

Met Gln Ile His Glu Arg Leu Ser Ala Leu Glu Leu Thr Thr Thr Ser
                20                  25                  30

Leu Asn Asp Ser Val Asn Thr Ala Leu Ser Lys Val Thr Asp Leu Ser
                35                  40                  45

Gly Ser Leu Asp Asn Met Ala Val Ser Leu Ala Glu Thr Lys Val Glu
 50                  55                  60

Leu Ser Ser Leu Ser Ser Ala Val Gln Gly Leu Arg Thr Ser Leu Glu
 65                  70                  75                  80

Ser Ser Ala Ser Glu Leu Ala Ser Leu Ser Ser Leu Val Arg Asn His
                85                  90                  95

Gly Ser Ala Ile Ser Asp Leu Gln Lys Glu Gly Gln Val Leu Leu Val
                100                 105                 110

Glu Val Ser Asn Leu Lys Ser Ser Val Ser Ser Gln Gly Leu Thr Ile
```

```
            115                 120                 125
Ser Asn Leu Glu Arg Arg Val Gln Ala Leu Glu Gly Gly Ser Ser Thr
130                 135                 140

Thr Leu Ser Phe Ala Asp Pro Leu Lys Leu Glu Asp Gly Thr Val Ser
145                 150                 155                 160

Leu Glu Leu Asp Pro Tyr Phe Cys Ser Val Ser Arg Asn Leu Thr Ser
                165                 170                 175

Tyr Ser Ala Gly Ala Gln Leu Met Gln Phe Gln Trp Ser Val Lys Gly
            180                 185                 190

Glu Asp Gly Ala Ala Asn Ser Ile Asp Met Asp Val Asn Ala His Ser
        195                 200                 205

His Gly Pro Arg Thr Asp Tyr Leu Met Ser Thr Lys Gln Ser Leu Thr
    210                 215                 220

Val Thr Thr Ser Pro Ala Thr Leu Val Phe Glu Leu Asp Arg Ile Thr
225                 230                 235                 240

Ser Leu Pro Ser Asp Leu Ser Arg Leu Ile Pro Cys His Gly Phe Gln
                245                 250                 255

Gln Ala Thr Phe Pro Val Asp Ile Ser Phe Gln Arg Asp Gly Val Ser
            260                 265                 270

His Thr Tyr Gln Val Tyr Gly Lys Tyr Val Ser Ser Arg Val Phe Lys
        275                 280                 285

Ile Thr Phe Ser Pro Gly Ser Ser Gly Pro Ala Val Val Gln Phe Leu
    290                 295                 300

Thr
305

<210> SEQ ID NO 14
<211> LENGTH: 312
<212> TYPE: PRT
<213> ORGANISM: Avian reovirus

<400> SEQUENCE: 14

Gln Arg Arg Glu Val Val Gly Leu Ile Leu Ser Leu Thr Ser Ser Val
1               5                   10                  15

Thr Ile Ser Pro Gly Asp Leu Thr Gln Ile His Glu Arg Leu Ser Ala
            20                  25                  30

Leu Glu Leu Thr Thr Thr Ser Leu Asn Asp Ser Val Asn Thr Ala Leu
        35                  40                  45

Ser Lys Val Thr Asp Leu Ser Gly Ser Leu Asp Asn Met Ala Val Ser
    50                  55                  60

Leu Ala Glu Thr Lys Val Glu Leu Ser Ser Leu Ser Ser Ala Val Gln
65                  70                  75                  80

Gly Leu Arg Thr Ser Leu Glu Ser Ser Ala Ser Glu Leu Ala Ser Leu
                85                  90                  95

Ser Ser Leu Val Arg Asn His Gly Ser Ala Ile Ser Asp Leu Gln Lys
            100                 105                 110

Glu Gly Gln Val Leu Leu Val Glu Val Ser Asn Leu Lys Ser Ser Val
        115                 120                 125

Ser Ser Gln Gly Leu Thr Ile Ser Asn Leu Glu Arg Arg Val Gln Ala
    130                 135                 140

Leu Glu Gly Gly Ser Ser Thr Thr Leu Ser Phe Ala Asp Pro Leu Lys
145                 150                 155                 160

Leu Glu Asp Gly Thr Val Ser Leu Glu Leu Asp Pro Tyr Phe Cys Ser
                165                 170                 175
```

```
Val Ser Arg Asn Leu Thr Ser Tyr Ser Ala Gly Ala Gln Leu Met Gln
            180                 185                 190

Phe Gln Trp Ser Val Lys Gly Glu Asp Gly Ala Ala Asn Ser Ile Asp
            195                 200                 205

Met Asp Val Asn Ala His Ser His Gly Pro Arg Thr Asp Tyr Leu Met
            210                 215                 220

Ser Thr Lys Gln Ser Leu Thr Val Thr Thr Ser Pro Ala Thr Leu Val
225                 230                 235                 240

Phe Glu Leu Asp Arg Ile Thr Ser Leu Pro Ser Asp Leu Ser Arg Leu
                    245                 250                 255

Ile Pro Cys His Gly Phe Gln Gln Ala Thr Phe Pro Val Asp Ile Ser
            260                 265                 270

Phe Gln Arg Asp Gly Val Ser His Thr Tyr Gln Val Tyr Gly Lys Tyr
            275                 280                 285

Val Ser Ser Arg Val Phe Lys Ile Thr Phe Ser Pro Gly Ser Ser Gly
            290                 295                 300

Pro Ala Val Val Gln Phe Leu Thr
305                 310

<210> SEQ ID NO 15
<211> LENGTH: 260
<212> TYPE: PRT
<213> ORGANISM: Avian reovirus

<400> SEQUENCE: 15

Val Val Gly Leu Ile Leu Ser Leu Thr Ser Ser Val Thr Ile Ser Pro
1               5                   10                  15

Gly Asp Leu Met Gln Ile His Glu Arg Leu Ser Ala Leu Glu Ser Ala
            20                  25                  30

Ile Thr Ser Leu Asn Glu Ser Val Asp Thr Ala Leu Ser Lys Leu Val
            35                  40                  45

Asp Leu Ser Gly Ser Leu Asp Ser Met Ala Val Ser Leu Ala Glu Thr
        50                  55                  60

Lys Val Glu Leu His Ser Leu Ser Ser Asp Val Lys Gly Leu Arg Thr
65                  70                  75                  80

Ser Leu Asp Ser Ser Ala Ser Glu Leu Ala Ser Leu Ser Ser Leu Val
                85                  90                  95

His Asp His Gly Ser Ser Ile Ser Asp Leu Gln Lys Gly Ser Arg Val
            100                 105                 110

Leu Ser Val Glu Val Asp Asn Leu Lys Ser Ser Val Ser Ser Gln Gly
            115                 120                 125

Leu Met Ile Ser Ser Leu Glu Ser Arg Val Gln Ala Leu Glu Gly Gly
        130                 135                 140

Pro Gly Thr Asn Leu Ser Phe Ala Asp Pro Leu Lys Leu Glu Asp Gly
145                 150                 155                 160

Thr Val Ser Leu Glu Leu Asp Pro Tyr Phe Cys Ser Val Ser Arg Asn
                165                 170                 175

Leu Thr Ser Tyr Ser Ala Asp Ala Gln Leu Met Gln Phe Gln Trp Ser
            180                 185                 190

Ala Lys Gly Glu Asp Gly Ala Ala Asn Ser Ile Asp Met Asp Val Asn
            195                 200                 205

Ala His Ser His Gly Ser Arg Thr Asp Tyr Leu Met Ser Thr Lys Gln
        210                 215                 220

Ser Leu Thr Val Thr Thr Ser Pro Ala Thr Leu Val Phe Glu Leu Gly
225                 230                 235                 240
```

Arg Ile Thr Ala Leu Pro Ser Asp Leu Ser Arg Leu Ile Pro Cys His
            245                 250                 255

Gly Phe Gln Gln
            260

<210> SEQ ID NO 16
<211> LENGTH: 254
<212> TYPE: PRT
<213> ORGANISM: Avian reovirus

<400> SEQUENCE: 16

Gln Arg Arg Glu Val Val Gly Leu Ile Leu Ser Leu Thr Ser Ser Val
1               5                   10                  15

Thr Ile Ser Pro Gly Asp Leu Met Arg Ile His Glu Arg Leu Ser Ala
            20                  25                  30

Leu Glu Leu Thr Thr Thr Ser Leu Asn Asp Ser Val Asn Thr Ala Leu
        35                  40                  45

Ser Lys Val Thr Asp Leu Ser Gly Ser Leu Asp Asn Met Ala Val Ser
    50                  55                  60

Leu Ala Glu Thr Lys Val Glu Leu Ser Ser Leu Ser Ser Ala Val Gln
65                  70                  75                  80

Gly Leu Arg Thr Ser Leu Glu Ser Ser Ala Ser Glu Leu Ala Ser Leu
                85                  90                  95

Ser Ser Leu Val Arg Asn His Gly Ser Ala Ile Ser Asp Leu Gln Lys
            100                 105                 110

Glu Gly Gln Ala Leu Leu Val Glu Val Ser Asn Leu Lys Ser Ser Val
        115                 120                 125

Ser Ser Gln Gly Leu Thr Ile Ser Asn Leu Glu Arg Arg Val Gln Ala
    130                 135                 140

Leu Glu Gly Gly Ser Ser Thr Thr Leu Ser Phe Ala Asp Pro Leu Lys
145                 150                 155                 160

Leu Glu Asp Gly Thr Val Ser Leu Glu Leu Asp Pro Tyr Phe Cys Ser
                165                 170                 175

Val Ser Arg Asn Leu Thr Ser Tyr Ser Ala Gly Ala Gln Leu Met Gln
            180                 185                 190

Phe Gln Trp Ser Val Lys Gly Glu Asp Gly Ala Ala Asn Ser Ile Asp
        195                 200                 205

Met Asp Val Asn Ala His Ser His Gly Pro Arg Thr Asp Tyr Leu Met
    210                 215                 220

Ser Thr Lys Gln Ser Leu Thr Val Thr Thr Ser Pro Ala Thr Leu Val
225                 230                 235                 240

Phe Glu Leu Asp Arg Ile Thr Ser Leu Pro Ser Asp Leu Ser
                245                 250

<210> SEQ ID NO 17
<211> LENGTH: 267
<212> TYPE: PRT
<213> ORGANISM: Avian reovirus

<400> SEQUENCE: 17

Gly Asp Leu Thr Thr Ile Tyr Glu Arg Leu Leu Lys Leu Asp Ser Ser
1               5                   10                  15

Val Glu Ser Leu Thr Ile Ser Val Gly Asp Leu Ser Arg Lys Leu Ser
            20                  25                  30

Glu Leu Glu Val Asp Leu Gln Asn Ile Asp Ser Ser Met His Gln Leu
        35                  40                  45

```
Thr Ser Ser Leu Thr Thr Leu Ser Glu Glu Val Arg Gln Leu Arg Ser
    50                  55                  60

Ala Val Gly Asp Asn Thr Asp Ser Ile Ser Ser Leu Ser Thr Met Val
 65                  70                  75                  80

Ser Asp His Gln Gln Leu Leu Ala Asp Leu Arg Thr Ser Leu Asn Ala
                85                  90                  95

Asn Val Thr Asp Ile Thr Asn Leu Lys Gly Val Thr Thr Leu Ser
            100                 105                 110

Leu Thr Val Thr Asp Leu Glu Lys Arg Leu Lys Val Glu Ser Gly
            115                 120                 125

Ser Ser Ser Ser Leu Glu Phe Thr Ser Pro Leu Ser Leu Thr Asp Gly
    130                 135                 140

Val Val Ser Leu Asn Met Asp Pro Tyr Phe Cys Ser Asp Asn His Ala
145                 150                 155                 160

Leu Thr Ser Tyr Ser Ser Asp Ala Gln Leu Met Gln Phe Gln Trp Leu
                165                 170                 175

Ala Arg Gly Asp Asp Gly Ser Ala Gly Ser Val Glu Met Leu Val Asn
                180                 185                 190

Ala His Cys His Gly Arg Arg Thr Asp Tyr Met Met Ser Thr Thr Glu
                195                 200                 205

Asn Leu Thr Val Thr Gly Asn Ser Thr Ser Leu Val Phe Ser Leu Asp
    210                 215                 220

Tyr Ile Thr Lys Pro Pro Ser Asp Met Ser Arg Leu Val Pro Arg Ala
225                 230                 235                 240

Gly Phe Gln Ala Ala Ser Phe Pro Val Asp Val Ser Phe Thr Arg Asp
                245                 250                 255

Thr Thr Thr His Ala Tyr Gln Val Tyr Gly Ala
                260                 265

<210> SEQ ID NO 18
<211> LENGTH: 267
<212> TYPE: PRT
<213> ORGANISM: Avian reovirus

<400> SEQUENCE: 18

Gly Asp Leu Thr Thr Ile Tyr Glu Arg Leu Leu Lys Leu Asp Ser Ser
1               5                   10                  15

Val Glu Ser Leu Thr Ile Ser Val Gly Asp Leu Ser Arg Lys Leu Ser
                20                  25                  30

Glu Leu Glu Val Asp Leu Gln Asn Ile Asp Ser Ser Met His Gln Leu
            35                  40                  45

Thr Ser Ser Leu Thr Thr Leu Ser Glu Glu Val Arg Gln Leu Arg Ser
    50                  55                  60

Ala Val Gly Asp Asn Thr Asp Ser Ile Ser Ser Leu Ser Thr Met Val
 65                  70                  75                  80

Ser Asp His Gln Gln Leu Leu Ala Asp Leu Gln Thr Ser Leu Asn Ala
                85                  90                  95

Asn Val Thr Asp Ile Thr Asn Leu Lys Gly Ser Val Thr Thr Leu Ser
            100                 105                 110

Leu Thr Val Thr Asp Leu Glu Lys Arg Leu Lys Val Val Glu Ser Gly
            115                 120                 125

Ser Ser Ser Ser Leu Glu Phe Thr Ser Pro Leu Ser Leu Thr Asp Gly
    130                 135                 140

Val Val Ser Leu Asn Met Asp Pro Tyr Phe Cys Ser Asp Asn His Ala
```

```
              145                 150                 155                 160
Leu Thr Ser Tyr Ser Ala Gly Ala Gln Leu Met Gln Phe Gln Trp Leu
                165                 170                 175
Ala Arg Gly Asp Asp Gly Ser Ala Gly Ser Val Glu Met Leu Val Asn
                180                 185                 190
Ala His Cys His Gly Arg Arg Thr Asp Tyr Met Met Ser Thr Thr Glu
                195                 200                 205
Asn Leu Thr Val Thr Gly Asn Ser Thr Ser Leu Val Phe Ser Leu Asp
                210                 215                 220
Tyr Ile Thr Lys Pro Pro Ser Asp Met Ser Arg Leu Val Pro Arg Ala
225                 230                 235                 240
Gly Phe Gln Ala Ala Ser Phe Pro Val Asp Val Ser Phe Thr Arg Asp
                245                 250                 255
Thr Thr Thr His Ala Tyr Gln Val Tyr Gly Ala
                260                 265

<210> SEQ ID NO 19
<211> LENGTH: 267
<212> TYPE: PRT
<213> ORGANISM: Avian reovirus

<400> SEQUENCE: 19

Gly Asp Leu Thr Thr Ile Tyr Glu Arg Leu Leu Lys Leu Asp Ser Ser
1               5                   10                  15
Val Glu Ser Leu Thr Ile Ser Ala Gly Asp Leu Ser Arg Arg Phe Ser
                20                  25                  30
Glu Leu Glu Val Asp Leu Gln Asn Val Asn Ser Ser Met His Gln Leu
                35                  40                  45
Thr Ser Ser Leu Thr Thr Leu Ser Glu Glu Ala Arg Gln Leu Arg Ser
50                  55                  60
Ala Val Ser Asp Asn Thr Ala Ser Ile Ser Ser Leu Ser Thr Met Val
65                  70                  75                  80
Ser Gly His Gln Gln Leu Leu Ala Asp Leu Gln Thr Ser Leu Asn Ala
                85                  90                  95
Asn Val Thr Asp Ile Ala Asn Leu Lys Gly Ser Val Thr Thr Leu Ser
                100                 105                 110
Leu Thr Val Thr Asp Leu Glu Lys Arg Leu Lys Val Val Glu Ser Gly
                115                 120                 125
Ser Ser Ser Ser Leu Glu Phe Thr Ser Pro Leu Ser Leu Thr Asp Gly
130                 135                 140
Val Val Ser Leu Asn Met Asp Pro Tyr Phe Cys Ser Asp Asn His Ala
145                 150                 155                 160
Leu Thr Ser Tyr Ser Ser Asp Ala Gln Leu Met Gln Phe Gln Trp Leu
                165                 170                 175
Ala Arg Gly Asp Asp Gly Ser Ala Gly Ser Val Glu Met Leu Val Asn
                180                 185                 190
Ala His Cys His Gly Arg Arg Thr Asp Tyr Met Met Ser Thr Thr Glu
                195                 200                 205
Asn Leu Thr Val Thr Gly Asn Ser Thr Ser Leu Val Phe Ser Leu Asp
                210                 215                 220
Tyr Ile Thr Lys Pro Pro Ser Asp Met Ser Arg Leu Val Pro Arg Ala
225                 230                 235                 240
Gly Phe Gln Ala Ala Ser Phe Pro Val Asp Val Ser Phe Thr Arg Asp
                245                 250                 255
```

-continued

```
Thr Thr Thr His Ala Tyr Gln Val Tyr Gly Ala
            260                 265

<210> SEQ ID NO 20
<211> LENGTH: 267
<212> TYPE: PRT
<213> ORGANISM: Avian reovirus

<400> SEQUENCE: 20

Gly Asp Leu Thr Thr Ile Tyr Glu Arg Leu Leu Lys Leu Asp Ser Ser
1               5                   10                  15

Val Glu Ser Leu Thr Ile Ser Ala Gly Asp Leu Ser Arg Arg Phe Ser
            20                  25                  30

Glu Leu Glu Val Asp Leu Gln Asn Val Asn Ser Ser Met His Gln Leu
        35                  40                  45

Thr Ser Ser Leu Thr Thr Leu Ser Glu Glu Ala Arg Gln Leu Arg Ser
    50                  55                  60

Ala Val Ser Asp Asn Thr Ala Ser Ile Ser Ser Leu Ser Thr Met Val
65                  70                  75                  80

Ser Gly His Gln Gln Leu Leu Ala Asp Leu Gln Thr Ser Leu Asn Ala
                85                  90                  95

Asn Val Thr Asp Ile Ala Asn Leu Lys Gly Ser Val Thr Thr Leu Ser
            100                 105                 110

Leu Thr Val Thr Asp Leu Glu Lys Arg Leu Lys Val Val Glu Ser Gly
        115                 120                 125

Ser Ser Ser Ser Leu Glu Phe Thr Ser Pro Leu Ser Leu Thr Asp Gly
    130                 135                 140

Val Val Ser Leu Asn Met Asp Pro Tyr Phe Cys Ser Asp Asn His Ala
145                 150                 155                 160

Leu Thr Ser Tyr Ser Ser Asp Ala Gln Leu Met Arg Phe Gln Trp Leu
                165                 170                 175

Ala Arg Gly Asp Asp Gly Ser Ala Gly Ser Val Glu Met Leu Val Asn
            180                 185                 190

Ala His Cys His Gly Arg Arg Thr Asp Tyr Met Met Ser Thr Thr Glu
        195                 200                 205

Asn Leu Thr Val Thr Gly Asn Ser Thr Ser Leu Val Phe Ser Leu Asp
    210                 215                 220

Tyr Ile Thr Lys Pro Pro Ser Asp Met Ser Arg Leu Val Pro Arg Ala
225                 230                 235                 240

Gly Phe Gln Ala Ala Ser Phe Pro Val Asp Val Ser Phe Thr Arg Asp
                245                 250                 255

Thr Thr Thr His Ala Tyr Gln Val Tyr Gly Ala
            260                 265

<210> SEQ ID NO 21
<211> LENGTH: 267
<212> TYPE: PRT
<213> ORGANISM: Avian reovirus

<400> SEQUENCE: 21

Gly Asp Leu Ala Ser Ile His Asp Arg Leu Leu Lys Leu Asp Ser Thr
1               5                   10                  15

Val Glu Ser Leu Thr Ala Ser Val Gly Asp Leu Ser Gln Lys Cys Ile
            20                  25                  30

Asp Leu Glu Ser Asn Phe Gln Ser Val Glu Ser Ser Leu Gly Gln Val
        35                  40                  45
```

Thr Ser Ser Leu Thr Asp Leu Ser Thr Glu Ile Arg Gln Leu Arg Leu
    50                  55                  60

Ser Leu Asn Asp Ile Thr Ser Ser Met Ala Ser Leu Ser Thr Thr Val
 65                  70                  75                  80

Ser Asp His Asp Asn Ser Leu Ser Thr Leu Arg Val Ser Val Gln Thr
                 85                  90                  95

Asn Val Thr Asp Ile Ala Asn Leu Lys Ser Ser Val Asn Thr Leu Ser
            100                 105                 110

Leu Thr Val Ala Asp Leu Glu Lys Arg Leu Gly Val Val Glu Ser Gly
            115                 120                 125

Ser Ser Ser Ser Leu Arg Phe Ser Ser Pro Leu Ser Leu Asn Asn Gly
130                 135                 140

Val Val Ser Leu Asp Met Asp Pro Tyr Phe Cys Ser Asp Asn His Ala
145                 150                 155                 160

Leu Thr Ser Tyr Ser Ser Asp Ala Gln Leu Met Gln Phe Gln Trp Leu
                165                 170                 175

Ala Arg Gly Asp Asp Gly Ser Ser Gly Ser Val Glu Met Leu Val Asn
            180                 185                 190

Ala His Cys His Gly Arg Arg Thr Asp Tyr Met Met Ser Thr Thr Glu
            195                 200                 205

Asn Leu Thr Val Thr Gly Asn Ser Thr Ser Leu Val Phe Ser Leu Asp
210                 215                 220

Tyr Ile Thr Arg Pro Pro Ser Asp Met Ser Arg Leu Ile Pro Arg Ala
225                 230                 235                 240

Gly Phe Gln Ala Ala Ser Phe Pro Val Asp Val Ser Phe Thr Arg Asp
                245                 250                 255

Thr Thr Thr His Ala Tyr Gln Val Tyr Gly Ala
            260                 265

<210> SEQ ID NO 22
<211> LENGTH: 296
<212> TYPE: PRT
<213> ORGANISM: Avian reovirus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Tyr Cys Ser Leu Thr Ser Xaa Arg Glu Tyr Lys Leu Trp Glu His Leu
1               5                   10                  15

Ala Ser Ile His Asp Arg Leu Leu Lys Leu Asp Ser Thr Val Glu Ser
            20                  25                  30

Leu Thr Ala Ser Val Gly Asp Leu Ser Gln Lys Cys Ile Asp Leu Glu
        35                  40                  45

Ser Asn Phe Gln Ser Val Glu Ser Ser Leu Gly Gln Val Thr Ser Ser
 50                  55                  60

Leu Thr Asp Leu Ser Thr Glu Ile Arg Gln Leu Arg Leu Ser Leu Asn
 65                  70                  75                  80

Asp Ile Ala Ser Ser Met Ala Ser Leu Ser Thr Thr Val Ser Asp His
                 85                  90                  95

Asp Asn Ser Leu Ser Thr Leu Arg Val Ser Val Gln Thr Asn Val Thr
            100                 105                 110

Asp Ile Ala Asn Leu Lys Ser Ser Val Ser Thr Leu Ser Leu Thr Val
            115                 120                 125

Ala Asp Leu Glu Lys Arg Leu Gly Val Val Glu Ser Gly Ser Ser Ser

```
                130                 135                 140
Ser Leu Arg Phe Ser Ser Pro Leu Ser Leu Asn Asn Gly Val Val Ser
145                 150                 155                 160

Leu Asp Met Asp Pro Tyr Phe Cys Ser Asp Asn His Ser Leu Thr Ser
                165                 170                 175

Tyr Ser Ser Asp Ala Gln Leu Met Gln Phe Gln Trp Leu Ala Arg Gly
            180                 185                 190

Asp Asp Gly Ser Ser Gly Ser Val Glu Met Leu Val Asn Ala His Cys
            195                 200                 205

His Gly Arg Arg Thr Asp Tyr Met Met Ser Thr Thr Glu Asn Leu Thr
        210                 215                 220

Val Thr Gly Asn Ser Thr Ser Leu Val Phe Ser Leu Asp Tyr Ile Thr
225                 230                 235                 240

Arg Pro Pro Ser Asp Met Ser Arg Leu Ile Pro Arg Ala Gly Phe Gln
                245                 250                 255

Ala Ala Ser Phe Pro Val Asp Val Ser Phe Thr Arg Asp Thr Thr Thr
                260                 265                 270

His Ala Tyr Gln Val Tyr Gly Ala Tyr Thr Thr Pro Arg Leu Ser Arg
            275                 280                 285

Leu Arg Phe Leu Thr Gly Gly Thr
        290                 295

<210> SEQ ID NO 23
<211> LENGTH: 267
<212> TYPE: PRT
<213> ORGANISM: Avian reovirus

<400> SEQUENCE: 23

Gly Asp Leu Thr Pro Ile Tyr Glu Arg Leu Thr Asn Leu Glu Ala Ser
1               5                   10                  15

Thr Glu Leu Leu His Arg Ser Ile Ser Asp Ile Ser Thr Thr Val Ser
            20                  25                  30

Asn Ile Ser Ala Ser Leu Gln Asp Met Thr His Thr Leu Asp Asp Val
        35                  40                  45

Thr Ala Asn Leu Asp Gly Leu Arg Thr Thr Val Thr Ala Leu Gln Asp
    50                  55                  60

Ser Val Ser Ile Leu Ser Thr Asn Val Thr Asp Leu Thr Asn Thr Ser
65                  70                  75                  80

Ser Ala His Ala Ala Thr Leu Ser Ser Leu Gln Thr Thr Val Asp Gly
                85                  90                  95

Asn Ser Thr Ala Ile Ser Asn Leu Lys Ser Asp Val Ser Ser Asn Gly
            100                 105                 110

Leu Ala Ile Thr Asp Leu Gln Asp Arg Val Lys Ser Leu Glu Ser Thr
        115                 120                 125

Ala Ser His Gly Leu Ser Phe Ser Pro Pro Leu Ser Val Ala Asp Gly
    130                 135                 140

Val Val Ser Leu Asp Met Asp Pro Tyr Phe Cys Ser Gln Arg Val Ser
145                 150                 155                 160

Leu Thr Ser Tyr Pro Ala Glu Ala Gln Leu Met Gln Phe Arg Trp Met
                165                 170                 175

Ala Arg Gly Thr Asn Gly Ser Ser Asp Thr Ile Asp Met Thr Val Asn
            180                 185                 190

Ala His Cys His Gly Arg Arg Thr Asp Tyr Met Met Ser Ser Thr Gly
        195                 200                 205
```

Asn Leu Thr Val Thr Ser Asn Val Val Leu Leu Thr Phe Asp Leu Ser
        210                 215                 220

Asp Ile Thr His Ile Pro Ser Asp Leu Ala Arg Leu Val Pro Ser Ala
225                 230                 235                 240

Gly Phe Gln Ala Ala Ser Phe Pro Val Asp Val Ser Phe Thr Arg Asp
                245                 250                 255

Ser Ala Thr His Ala Tyr Gln Ala Tyr Gly Val
            260                 265

<210> SEQ ID NO 24
<211> LENGTH: 267
<212> TYPE: PRT
<213> ORGANISM: Avian reovirus

<400> SEQUENCE: 24

Gly Asp Leu Thr Thr Ile Tyr Glu Arg Leu Leu Lys Leu Asp Ser Ser
1               5                   10                  15

Val Glu Ser Leu Thr Ile Ser Val Gly Asp Leu Ser Arg Lys Leu Ser
            20                  25                  30

Glu Leu Glu Val Asp Leu Gln Asn Ile Asp Ser Ser Met His Gln Leu
        35                  40                  45

Thr Ser Ser Leu Thr Thr Leu Ser Glu Glu Val Arg Gln Leu Arg Ser
    50                  55                  60

Ala Val Gly Asp Asn Thr Asp Ser Ile Ser Ser Leu Ser Thr Met Val
65                  70                  75                  80

Ser Asp His Gln Gln Leu Leu Ala Asp Leu Gln Thr Ser Leu Asn Ala
                85                  90                  95

Asn Val Thr Asp Ile Thr Asn Leu Lys Gly Ser Val Thr Thr Leu Ser
                100                 105                 110

Leu Thr Val Thr Asp Leu Glu Lys Arg Leu Lys Val Val Glu Ser Gly
            115                 120                 125

Ser Ser Ser Ser Leu Glu Phe Thr Ser Pro Leu Ser Leu Thr Asp Gly
        130                 135                 140

Val Val Ser Leu Asn Met Asp Pro Tyr Phe Cys Ser Asp Asn His Ala
145                 150                 155                 160

Leu Thr Ser Tyr Ser Ala Gly Ala Gln Leu Met Gln Phe Gln Trp Leu
                165                 170                 175

Ala Arg Gly Asp Asp Gly Ser Ala Gly Ser Val Glu Met Leu Val Asn
            180                 185                 190

Ala His Cys His Gly Arg Arg Thr Asp Tyr Met Met Ser Thr Thr Glu
        195                 200                 205

Asn Leu Thr Val Thr Gly Asn Ser Thr Ser Leu Val Phe Ser Leu Asp
    210                 215                 220

Tyr Ile Thr Lys Pro Pro Ser Asp Met Ser Arg Leu Val Pro Arg Ala
225                 230                 235                 240

Gly Phe Gln Ala Ala Ser Phe Pro Val Asp Val Ser Phe Thr Arg Asp
                245                 250                 255

Thr Thr Thr His Ala Tyr Gln Val Tyr Gly Ala
            260                 265

<210> SEQ ID NO 25
<211> LENGTH: 267
<212> TYPE: PRT
<213> ORGANISM: Avian reovirus

<400> SEQUENCE: 25

```
Gly Asp Leu Thr Thr Ile Tyr Glu Arg Leu Leu Lys Leu Asp Ser Ser
1               5                   10                  15

Val Glu Ser Leu Thr Ile Ser Ala Gly Asp Leu Ser Arg Arg Phe Ser
            20                  25                  30

Glu Leu Glu Val Asp Leu Gln Asn Val Asn Ser Ser Met His Gln Leu
        35                  40                  45

Thr Ser Ser Leu Thr Thr Leu Ser Glu Glu Ala Arg Gln Leu Arg Ser
    50                  55                  60

Ala Val Ser Asp Asn Thr Ala Ser Ile Ser Leu Ser Thr Met Val
65                  70                  75                  80

Ser Gly His Gln Gln Leu Leu Ala Asp Leu Gln Thr Ser Leu Asn Ala
                85                  90                  95

Asn Val Thr Asp Ile Ala Asn Leu Lys Gly Ser Val Thr Thr Leu Ser
            100                 105                 110

Leu Thr Val Thr Asp Leu Glu Lys Arg Leu Lys Val Glu Ser Gly
        115                 120                 125

Ser Ser Ser Ser Leu Glu Phe Thr Ser Pro Leu Ser Leu Thr Asp Gly
    130                 135                 140

Val Val Ser Leu Asn Met Asp Pro Tyr Phe Cys Ser Asp Asn His Ala
145                 150                 155                 160

Leu Thr Ser Tyr Ser Ser Asp Ala Gln Leu Met Gln Phe Gln Trp Leu
                165                 170                 175

Ala Arg Gly Asp Asp Gly Ser Ala Gly Ser Val Glu Met Leu Val Asn
            180                 185                 190

Ala His Cys His Gly Arg Arg Thr Asp Tyr Met Met Ser Thr Thr Glu
        195                 200                 205

Asn Leu Thr Val Thr Gly Asn Ser Thr Ser Leu Val Phe Ser Leu Asp
    210                 215                 220

Tyr Ile Thr Lys Pro Pro Ser Asp Met Ser Arg Leu Val Pro Arg Ala
225                 230                 235                 240

Gly Phe Gln Ala Ala Ser Phe Pro Val Asp Val Ser Phe Thr Arg Asp
                245                 250                 255

Thr Thr Thr His Ala Tyr Gln Val Tyr Gly Ala
            260                 265

<210> SEQ ID NO 26
<211> LENGTH: 321
<212> TYPE: PRT
<213> ORGANISM: Avian reovirus

<400> SEQUENCE: 26

Leu Val Ile Ser Ser Gln Arg Arg Glu Val Val Ser Leu Ile Leu Ser
1               5                   10                  15

Leu Asn Ser Asn Val Thr Ile Asn Pro Gly Asp Leu Lys Ser Val Tyr
            20                  25                  30

Glu Arg Leu Asn Ser Leu Glu Ala Ser Thr Glu Ser Leu Arg Gln Ser
        35                  40                  45

Val Ser Gly Met Ser Val Thr Leu Ser Asp Leu Ser Ala Asp Leu Gln
    50                  55                  60

Asp Thr Thr Arg Ala Leu Asp Asp Val Thr Val Thr Leu Asn Asn Leu
65                  70                  75                  80

Ser Ala Thr Ile Thr Ala Leu Gln Ser Ser Val Thr Thr Leu Ser Ala
                85                  90                  95

Thr Val Asp Glu Leu Thr Asn Thr Ser Ser Ala His Ser Gly Met Leu
            100                 105                 110
```

-continued

Ser Ser Leu Gln Thr Ile Ile Asn Gly Asn Ser Ser Ala Ile Ser Asn
            115                 120                 125

Leu Arg Asn Asp Val Ser Ala Ser Gly Leu Asn Ile Thr Asp Leu Gln
130                 135                 140

Asn Arg Val Lys Ser Leu Glu Ser Asp Thr Ser His Gly Leu Ser Phe
145                 150                 155                 160

Ser Pro Pro Leu Ser Val Ala Asp Gly Val Val Ser Leu Asp Met Asp
                165                 170                 175

Pro Tyr Phe Cys Ser Gln Arg Val Ser Leu Thr Ser Tyr Ser Ala Glu
            180                 185                 190

Ala Arg Leu Met Gln Phe Gln Trp Val Ala Lys Gly Thr Ser Gly Ser
            195                 200                 205

Ser Asp Thr Ile Asp Met Thr Val Asn Ala His Cys His Gly Arg Arg
210                 215                 220

Thr Asp Tyr Met Met Ser Ser Thr Gly Gly Leu Thr Val Thr Ser Asn
225                 230                 235                 240

Ala Val Ser Leu Thr Phe Asp Leu Ser Tyr Ile Thr Asn Met Pro Ser
                245                 250                 255

Asp Leu Ser Arg Leu Ile Pro Ser Ala Gly Phe Gln Val Ala Ser Phe
            260                 265                 270

Pro Val Asp Val Ser Phe Thr Arg Glu Ser Ser Thr His Thr Tyr Gln
            275                 280                 285

Val Tyr Gly Ala Tyr Ser Ser Ala Arg Val Phe Thr Ile Thr Phe Pro
            290                 295                 300

Thr Gly Gly Asn Gly Thr Ser Asn Ile Arg Phe Leu Thr Val Arg Thr
305                 310                 315                 320

Gly

<210> SEQ ID NO 27
<211> LENGTH: 294
<212> TYPE: PRT
<213> ORGANISM: Avian reovirus

<400> SEQUENCE: 27

Trp Ile Asp Thr Val Asp Phe Glu Arg Asp Tyr Lys Ser Trp Arg
1               5                   10                  15

Phe Asp Ala Asn Pro Glu Arg Leu Ser Ala Leu Glu Leu Thr Thr Thr
                20                  25                  30

Ser Leu Asn Asp Ser Val Asn Thr Ala Leu Ser Lys Val Thr Asp Leu
            35                  40                  45

Ser Gly Ser Leu Asp Asn Met Ala Val Ser Leu Ala Glu Thr Lys Val
50                  55                  60

Glu Leu Ser Ser Leu Ser Val Val Gln Gly Leu Arg Thr Ser Leu
65                  70                  75                  80

Glu Ser Ser Ala Ser Glu Leu Ala Ser Leu Ser Leu Val Arg Asn
                85                  90                  95

His Gly Ser Ser Ile Ser Asp Leu Gln Lys Glu Gly Gln Ala Leu Leu
            100                 105                 110

Val Glu Val Asn Asn Leu Lys Ser Ser Val Ser Ser Gln Gly Leu Thr
            115                 120                 125

Ile Ser Asn Leu Glu Arg Arg Val Gln Ala Leu Glu Gly Gly Ser Ser
            130                 135                 140

Thr Thr Leu Ser Phe Ala Asp Pro Leu Lys Leu Glu Asp Gly Thr Val
145                 150                 155                 160

```
Ser Leu Glu Leu Asp Pro Tyr Phe Cys Ser Val Ser Arg Asn Leu Thr
                165                 170                 175

Ser Tyr Ser Ala Ser Ala Gln Leu Met Gln Phe Gln Trp Ser Val Lys
            180                 185                 190

Gly Glu Asp Gly Ala Ala Asn Ser Ile Asp Met Asp Val Asn Ala His
        195                 200                 205

Ser His Gly Pro Arg Thr Asp Tyr Leu Met Ser Thr Lys Gln Ser Leu
    210                 215                 220

Thr Val Thr Thr Ser Pro Ala Thr Leu Val Phe Glu Leu Asp Arg Ile
225                 230                 235                 240

Thr Ser Leu Pro Ser Asp Leu Ser Arg Leu Ile Pro Cys His Gly Phe
                245                 250                 255

Gln Gln Ala Thr Phe Pro Val Asp Ile Ser Phe Gln Arg Asp Gly Val
            260                 265                 270

Ser His Thr Tyr Gln Val Tyr Gly Lys Tyr Ala Ser Ser Arg Val Phe
        275                 280                 285

Lys Ile Thr Phe Ser Pro
    290

<210> SEQ ID NO 28
<211> LENGTH: 126
<212> TYPE: PRT
<213> ORGANISM: Avian reovirus

<400> SEQUENCE: 28

Asn Ile Lys Pro Gly Asp Leu Lys Ser Val Tyr Glu Arg Leu Thr Ser
1               5                   10                  15

Leu Glu Ala Ser Thr Glu Ser Leu Arg Gln Ser Val Ser Gly Met Ser
            20                  25                  30

Val Thr Leu Ser Asp Leu Ser Ala Asp Leu Gln Asp Thr Thr Arg Ala
        35                  40                  45

Leu Asp Asp Val Thr Val Thr Leu Asn Asn Leu Ser Ala Thr Ile Thr
    50                  55                  60

Ala Leu Gln Ser Ser Val Thr Thr Leu Ser Ala Thr Val Asp Glu Leu
65                  70                  75                  80

Thr Asn Thr Ser Ser Ala His Ser Gly Met Leu Ser Ser Leu Gln Thr
                85                  90                  95

Ile Ile Asn Gly Asn Ser Ser Ala Ile Ser Asn Leu Arg Asn Asp Val
            100                 105                 110

Ser Ala Ser Gly Leu Asn Ile Thr Asp Leu Gln Asp Arg Val
        115                 120                 125

<210> SEQ ID NO 29
<211> LENGTH: 116
<212> TYPE: PRT
<213> ORGANISM: Avian reovirus

<400> SEQUENCE: 29

Asp Ala Gln Leu Met Gln Phe Gln Trp Leu Ala Arg Gly Asp Asp Gly
1               5                   10                  15

Ser Ser Gly Ser Val Glu Met Leu Val Asn Ala His Cys His Gly Arg
            20                  25                  30

Arg Thr Asp Tyr Met Met Ser Thr Thr Glu Asn Leu Thr Val Thr Gly
        35                  40                  45

Asn Ser Thr Ser Leu Val Phe Ser Leu Asp Tyr Ile Thr Arg Pro Pro
    50                  55                  60
```

Ser Asp Met Ser Arg Leu Ile Pro Arg Ala Gly Phe Gln Ala Ala Ser
65                  70                  75                  80

Phe Pro Val Asp Val Ser Phe Thr Arg Asp Thr Thr His Ala Tyr
            85                  90                  95

Gln Val Tyr Gly Ala Tyr Thr Thr Pro Arg Leu Phe Lys Ile Thr Phe
            100                 105                 110

Pro Thr Gly Arg
        115

<210> SEQ ID NO 30
<211> LENGTH: 267
<212> TYPE: PRT
<213> ORGANISM: Avian reovirus

<400> SEQUENCE: 30

Gly Asp Leu Ile Pro Leu Tyr Glu Arg Leu Ser Ala Val Glu Lys Met
1               5                   10                  15

Cys Ala Thr Val Asn Asp Ser Leu Gly Arg Leu Thr Ser Leu Val Ser
            20                  25                  30

Glu Met Ser Ala Arg Ile Asp Ser Leu Ala Asp Thr Leu Gln Glu Asn
        35                  40                  45

Ala Ala Gly Leu Asp Gln Arg Ser Thr Val Thr Thr Leu Ser Val Ser
50                  55                  60

Leu Phe Asp Asp Leu Ser Gly Arg Val Ala Thr Leu Pro Leu Met Val
65                  70                  75                  80

Ser Asn Gln Glu Ser Gln Leu Pro Ser Ser Leu Pro Ser Val Asn Ala
            85                  90                  95

Leu Ser Thr Thr Cys Ser Asn Leu Gln Arg Asp Val Ser Ser Thr Ala
            100                 105                 110

Leu Thr Val Thr Ser Leu Gly Gln Arg Val Glu Ala Leu Glu Ser Gly
        115                 120                 125

Ala Gly Ser Asp Leu Thr Phe Met Ala Pro Leu Lys Val Asp Gly Lys
    130                 135                 140

Ser Val Ser Leu Asp Met Asp Pro Tyr Phe Cys Ser Glu Arg Thr Asn
145                 150                 155                 160

Leu Thr Ser Tyr Ser Ala Asn Ala Gln Leu Leu Gln Phe Gln Trp Leu
            165                 170                 175

Val Arg Ser Glu Gly Glu Ser Ser Asp Ser Ile Asp Met Asn Val Val
            180                 185                 190

Ala His Cys His Gly Arg Arg Thr Asp Tyr Leu Met Ser Thr His Asp
        195                 200                 205

Ser Leu Thr Val Val Gly Asn Ser Val Thr Leu Ile Phe Asn Leu Asp
    210                 215                 220

Phe Ile Thr Leu Lys Ala Ser Asp Tyr Ala Arg Leu Val Pro Cys His
225                 230                 235                 240

Gly Phe Gln Gln Ala Thr Phe Pro Val Asp Ile Ser Phe Thr Lys Gly
            245                 250                 255

Thr Ala Thr Gln Ser Tyr Gln Val Tyr Gly Ala
            260                 265

<210> SEQ ID NO 31
<211> LENGTH: 267
<212> TYPE: PRT
<213> ORGANISM: Avian reovirus

<400> SEQUENCE: 31

```
Gly Asp Leu Met Gln Ile His Glu Arg Leu Ser Ala Leu Glu Leu Thr
1               5                   10                  15

Thr Thr Ser Leu Asn Asp Ser Val Asn Thr Ala Leu Ser Lys Val Thr
                20                  25                  30

Asp Leu Ser Gly Ser Leu Asp Asn Met Ala Val Ser Leu Ala Glu Thr
            35                  40                  45

Glu Gly Glu Leu Ile Lys Leu Ser Ser Ala Val Gln Cys Leu Arg Thr
50                  55                  60

Ser Leu Asp His Leu Leu Gln Asn Trp Arg Leu Cys Pro His Trp Tyr
65                  70                  75                  80

Val Thr His Gly Ser Ser Ile Ser Asp Leu Gln Lys Glu Gly Gln Ala
                85                  90                  95

Leu Ser Ser Glu Val Asn Asn Leu Asn Leu His Val Ser Ser Gln Gly
                100                 105                 110

Leu Thr Val Ser Asn Leu Glu Arg Arg Val Gln Ala Leu Glu Gly Gly
            115                 120                 125

Ser Ser Thr Thr Leu Ser Phe Ala Asp Pro Leu Lys Phe Glu Asp Gly
    130                 135                 140

Thr Val Ser Leu Glu Leu Asp Pro Tyr Phe Cys Ser Val Ser Arg Asn
145                 150                 155                 160

Leu Thr Ser Tyr Ser Ala Gly Ala Gln Leu Met Gln Phe Gln Trp Ser
                165                 170                 175

Val Lys Gly Glu Asp Gly Ala Ala Asn Ser Ile Asp Met Asp Val Asn
                180                 185                 190

Ala His Ser His Gly Pro Arg Thr Asp Tyr Leu Met Ser Thr Lys Gln
            195                 200                 205

Ser Leu Thr Val Thr Ser Leu Leu Ala Thr Leu Val Phe Glu Leu Gly
    210                 215                 220

Arg Ile Thr Ser Leu Pro Ser Asp Leu Ser Arg Leu Ile Pro Cys His
225                 230                 235                 240

Gly Phe Gln Gln Ala Thr Phe Pro Val Asp Ile Ser Phe Gln Arg Asp
                245                 250                 255

Gly Val Ser His Thr Tyr Gln Val Tyr Gly Lys
                260                 265

<210> SEQ ID NO 32
<211> LENGTH: 162
<212> TYPE: PRT
<213> ORGANISM: Avian reovirus

<400> SEQUENCE: 32

Gln Ser Gln Arg Arg Glu Val Gly Gly Leu Ile Leu Ser Leu Thr Ser
1               5                   10                  15

Ser Val Thr Ile Ser Pro Gly Asp Leu Met Arg Ile His Glu Arg Leu
                20                  25                  30

Ser Ala Leu Glu Leu Thr Thr Thr Ser Leu Asn Asp Ser Val Asn Thr
            35                  40                  45

Ala Leu Ser Lys Val Thr Asp Leu Ser Gly Ser Leu Asp Asn Met Ala
50                  55                  60

Val Ser Leu Ala Glu Thr Lys Val Glu Leu Ser Ser Leu Ser Ser Ala
65                  70                  75                  80

Val Gln Gly Leu Arg Thr Ser Leu Glu Ser Ser Ala Ser Glu Leu Ala
                85                  90                  95

Ser Leu Ser Ser Leu Val Arg Asn His Gly Ser Ala Ile Ser Asp Leu
```

-continued

```
            100                 105                 110
Gln Lys Glu Gly Gln Ala Leu Leu Val Glu Val Ser Asn Leu Lys Ser
        115                 120                 125

Ser Val Ser Ser Gln Gly Leu Thr Ile Ser Asn Leu Glu Arg Gln Val
    130                 135                 140

Gln Ala Leu Glu Gly Gly Ser Ser Thr Thr Leu Ser Phe Ala Asp Pro
145                 150                 155                 160

Leu Lys

<210> SEQ ID NO 33
<211> LENGTH: 229
<212> TYPE: PRT
<213> ORGANISM: Avian reovirus

<400> SEQUENCE: 33

Glu Arg Leu Ser Ala Leu Glu Ser Ala Ile Thr Ser Leu Asn Glu Ser
1               5                   10                  15

Val Asp Thr Ala Leu Ser Lys Leu Val Asp Leu Ser Gly Ser Leu Asp
            20                  25                  30

Ser Met Ala Val Ser Leu Ala Glu Thr Lys Val Glu Leu His Ser Leu
        35                  40                  45

Ser Ser Asp Val Lys Gly Leu Arg Thr Ser Leu Asp Ser Ser Ala Ser
    50                  55                  60

Glu Leu Ala Ser Leu Ser Ser Leu Val His Asp His Gly Ser Ser Ile
65                  70                  75                  80

Ser Asp Leu Gln Lys Gly Ser Arg Val Leu Ser Val Glu Val Asp Asn
                85                  90                  95

Leu Lys Ser Ser Val Ser Ser Gln Gly Leu Met Ile Ser Ser Leu Glu
            100                 105                 110

Ser Arg Val Gln Ala Leu Glu Gly Gly Pro Gly Thr Asn Leu Ser Phe
        115                 120                 125

Ala Asp Pro Leu Lys Leu Glu Asp Gly Thr Val Ser Leu Glu Leu Asp
    130                 135                 140

Pro Tyr Phe Cys Ser Val Arg Arg Asn Leu Thr Ser Tyr Ser Ala Asp
145                 150                 155                 160

Ala Gln Leu Met Gln Phe Gln Trp Ser Ala Lys Gly Glu Asp Gly Ala
                165                 170                 175

Ala Asn Ser Ile Asp Met Asp Val Asn Ala His Ser His Gly Ser Arg
            180                 185                 190

Thr Asp Tyr Leu Met Ser Thr Lys Gln Ser Leu Thr Val Thr Thr Ser
        195                 200                 205

Pro Ala Thr Leu Val Phe Glu Leu Asp Arg Ile Thr Ala Leu Pro Ser
    210                 215                 220

Asp Phe Ser Ser Leu
225

<210> SEQ ID NO 34
<211> LENGTH: 302
<212> TYPE: PRT
<213> ORGANISM: Avian reovirus

<400> SEQUENCE: 34

Ile Ser Pro Gly Asp Leu Val Pro Val Tyr Asp Arg Leu Ser Ala Val
1               5                   10                  15

Glu Ala Ala Tyr Ala Thr Leu Asn Ala Ser Val Gly Gln Leu Thr Ser
            20                  25                  30
```

```
Thr Met Ser Asp Leu Ser Ile Arg Leu Asp Asp Leu Ala Asn Ala Ile
        35                  40                  45

Gln Ser Thr Ser Thr Asp Leu Arg Asp Val Gln Ser Arg Val Ser Ala
    50                  55                  60

Leu Gln Thr Ser Val Asp Gly Ile Ser Ser Asp Val Ala Thr Leu Ser
65                  70                  75                  80

Gln Ser Leu Ser Thr His Gly Ser Gln Leu Ser Ala Leu Ser Ser Ser
                85                  90                  95

Val Ser Thr Leu Ser Thr Asp Met Ser Asn Ile Gln Arg Asp Val Ala
            100                 105                 110

Ser Ser Ala Leu Asn Val Ala Asp Leu Gln Arg Arg Val Thr Ala Leu
        115                 120                 125

Glu Ser Gly Ala Gly Ser Ser Leu Thr Phe Leu Ala Pro Leu Arg Ala
    130                 135                 140

Asp Gly Gly Ser Val Ser Leu Asp Met Asp Pro Tyr Phe Cys Ser Glu
145                 150                 155                 160

Arg Ser Asn Leu Thr Ser Tyr Ser Ala Ser Ala Gln Leu Leu Gln Phe
                165                 170                 175

Gln Trp Phe Val Arg Ser Glu Gly Gly Ser Ser Asp Ser Ile Asp Met
            180                 185                 190

Ser Val Val Ala His Cys His Gly Arg Arg Thr Asp Tyr Leu Met Ser
        195                 200                 205

Ser His Asp Ser Leu Thr Val Thr Gly Asn Ser Val Ser Leu Val Phe
    210                 215                 220

Asn Leu Asp Tyr Ile Thr Thr Ser Gly Val Asp Tyr Ala Arg Leu Ile
225                 230                 235                 240

Pro Cys His Gly Phe Gln Gln Ala Thr Phe Pro Val Asp Ile Ser Phe
                245                 250                 255

Thr Lys Asn Asp Ala Thr His Thr Tyr Gln Val Tyr Gly Ala Phe Asp
            260                 265                 270

Gly Pro Arg Ile Phe Lys Val Thr Phe Ser Pro Gly Glu Thr Ser Thr
        275                 280                 285

Thr Asn Ile Arg Phe Ile Thr Val Arg Thr Gly Ile Glu Ile
290                 295                 300
```

OPTIMIZED POLYPEPTIDE FOR A SUBUNIT VACCINE AGAINST AVIAN REOVIRUS

FIELD OF THE INVENTION

The present invention relates in general to vaccines against avian reovirus.

BACKGROUND OF THE INVENTION

Avian reovirus (ARV) is a member of the *Orthoreovirus* genus in the family Reoviridae. It is associated with a number of diseases, the most prominent being viral arthritis syndrome (tenosynovitis) which is characterized by swelling of the hock joints and lesions in the gastrocnemius tendons, and causes considerable economic loss to the poultry industry. Susceptibility to ARV occurs mostly in young (1-2 weeks of age) chickens. The control of viral tenosynovitis in broiler chicks is conferred by antibodies that are transferred to the progeny following vaccination of maternal flocks. The available live-attenuated and inactivated vaccines for ARV are based on the s1133 strain (van der Heide et al. 1983), as well as isolated strains belonging to a single serotype (Goldenberg et al. 2010). However, those vaccines are not effective against the diverse ARVs found in the field (Jones 2000; Goldenberg et al. 2010; Lublin et al. 2011).

Sequencing of the sigma C (SC) protein of ARV isolates for genetic characterization enabled their division into genotypes (Kant et al. 2003; Lublin et al. 2011; Goldenberg et al. 2010; Troxler et al. 2013). Vaccination based on a mixture of the four representatives of ARV genotypes conferred protection against all tested viruses from the four genotypes [Lublin et al. 2011; WO 2009/093251]. The outer capsid cell attachment protein SC of ARV, encoded by the S1 gene, is a relatively small protein of 326 amino acids (Benavente & Martinez-Costas 2007), a homotrimer with a tertiary structure consisting of two domains: the "head", which is located at the C-terminal end of the protein, and the "shaft", at the N terminus. The crystal structure of the C-terminal domain and of residues 117-326 has been resolved (Guardado Calvo et al. 2005; Guardado-Calvo et al. 2009). SC elicits reovirus-specific neutralizing antibodies (Shapouri et al. 1996; Grande et al. 1997), making it a suitable candidate for a recombinant subunit vaccine.

Indeed, efficient recombinant vaccines have been developed in the past for a number of viruses, including vaccines for hepatitis B (McAleer et al. 1984) and for papillomavirus (Valentino & Poronsky 2015) for humans, as well as infectious bursal disease (IBD) (Pitcovski et al. 2003) and egg drop syndrome (Fingerut et al. 2003) for chickens and hemorrhagic enteritis virus for turkeys (Pitcovski et al. 2005). SC has been expressed in various expression systems, including bacteria, baculovirus, yeast, plants and mammalian cells. Recombinant SC proteins have been used for diagnostics to distinguish between strains. Anti-SC antibodies have been shown to neutralize the virus in cell lines [28,31]. In a previous study, SC expressed in bacteria showed only weak immunogenicity (Goldenberg et al. 2011; Vasserman et al. 2004). There remains therefore a great need for an efficient vaccine against ARV.

SUMMARY OF INVENTION

In one aspect, the present invention is directed to an isolated polypeptide comprising, or essentially consisting of, an amino acid sequence corresponding to the amino acid residues forming a full or partial α-helical domain, the hinge domain, the β-triple spiral domain and a full or partial globular head domain of an avian reovirus sigma C protein, and lacking the amino acid sequence that is N-terminal to said α-helical domain.

In an additional aspect, the present invention provides a nucleic acid molecule comprising a nucleic acid sequence encoding at least one of the isolated polypeptides defined herein.

In another aspect, the present invention provides an expression vector comprising a control element, such as a promoter, operably linked to said nucleic acid molecule defined herein, wherein said expression vector is designed to replicate and express relevant genes in for example a bacterial, yeast or insect cell.

In a further aspect, the present invention provides a vaccine comprising at least one of the isolated polypeptides defined herein.

In still a further aspect, the present invention provides a vaccine comprising a mammalian expression vector, such as pcDNA3, comprising a control element, such as a promoter, operably linked to the nucleic acid molecule defined herein.

In yet an additional aspect, the present invention provides a viral vector, such as a recombinant Marek's disease (MD) virus, comprising a control element, such as a promoter, operably linked to the nucleic acid molecule defined herein.

In yet another aspect, the present invention is directed to any one of the vaccines or viral vectors defined herein, for use in vaccination of an avian species or for use in inducing an avian immune response conferring protection against avian reovirus.

In yet an additional aspect, the present invention is directed to a method for vaccinating an avian species against avian reovirus or for inducing an avian immune response conferring protection against avian reovirus, which comprises administering any one of the vaccines or viral vectors defined herein to a bird.

DETAILED DESCRIPTION OF THE INVENTION

Avian reovirus (ARV) mutates relatively fast and many variants exist in the field worldwide. Vaccines that protect against one genotype are inefficient against others (Lu et al. 2015; Vasserman et al. 2004; Goldenberg et al. 2010; Shapouri et al. 1995). Production of attenuated vaccine is a long process, and in the case of highly mutated viruses inefficient. Adaptation of vaccines to alterations in the field virus is by the use of inactivated vaccines that are produced by propagation of the virulent isolates in cell cultures or embryonated eggs and its subsequent inactivation. In the era of molecular biology, subunit vaccines may be produced by genetic engineering. In this method, only the relevant updated protein for induction of neutralizing antibodies is produced in an expression system. As shown previously [26,27], sigma C protein (SC) in its full 326-amino-acid form can be expressed in a bacterial expression system. However, although antibodies against s1133, a viral strain of ARV, do identify recombinant SC, a low titer of antibodies was obtained in response to immunization with this protein.

Figure 2:
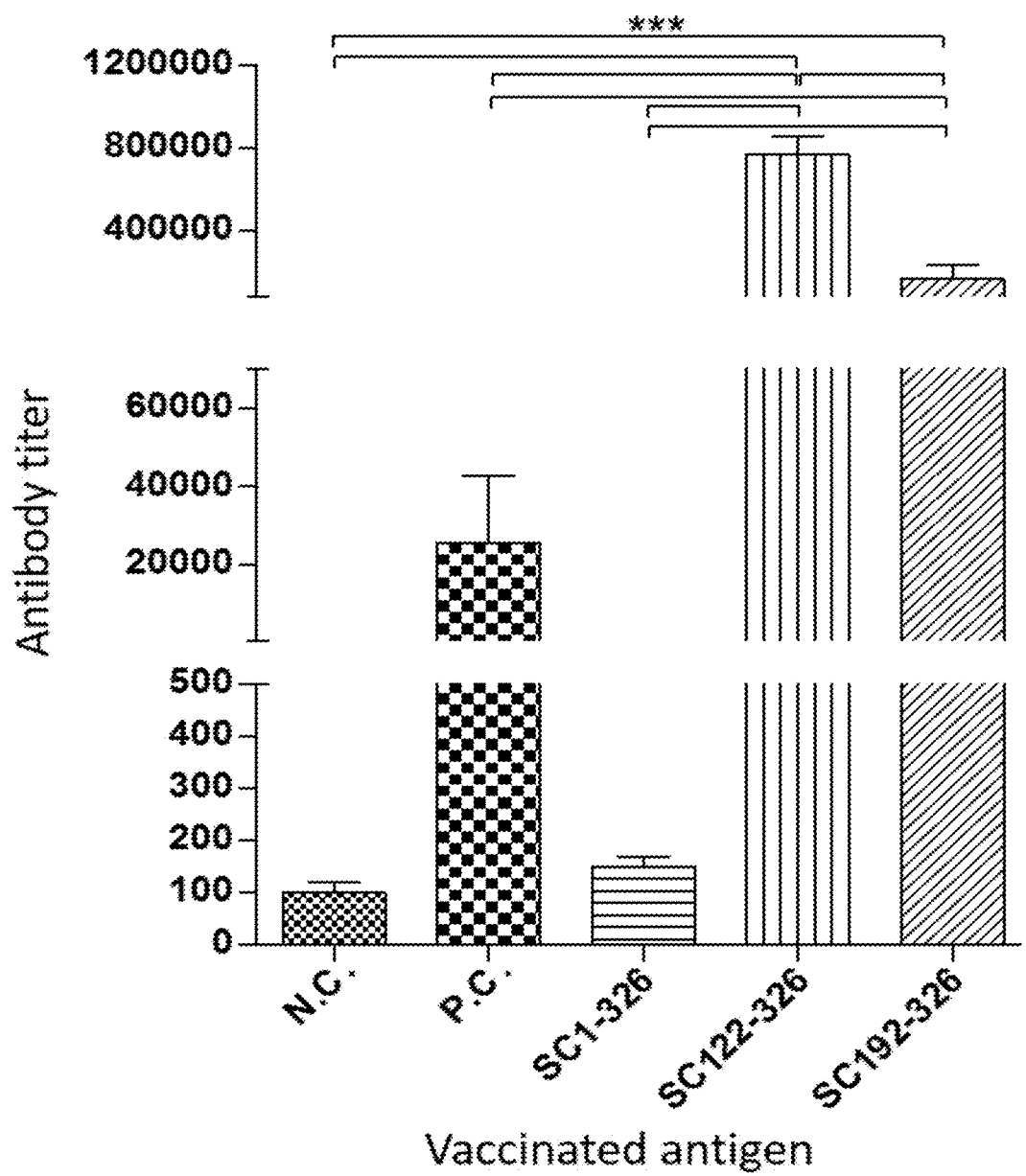
FIG. 2 depicts a bar graph showing antibody titers following vaccination with recombinant proteins SC1-326, SC122-326 and SC192-326, all of which are sequences of ARV s1133. Controls: N.C—negative control (birds vaccinated with PBS in adjuvant), P.C—positive control (injected with ARV s1133). *** Significantly different at $P<0.001$.
Figure 4:
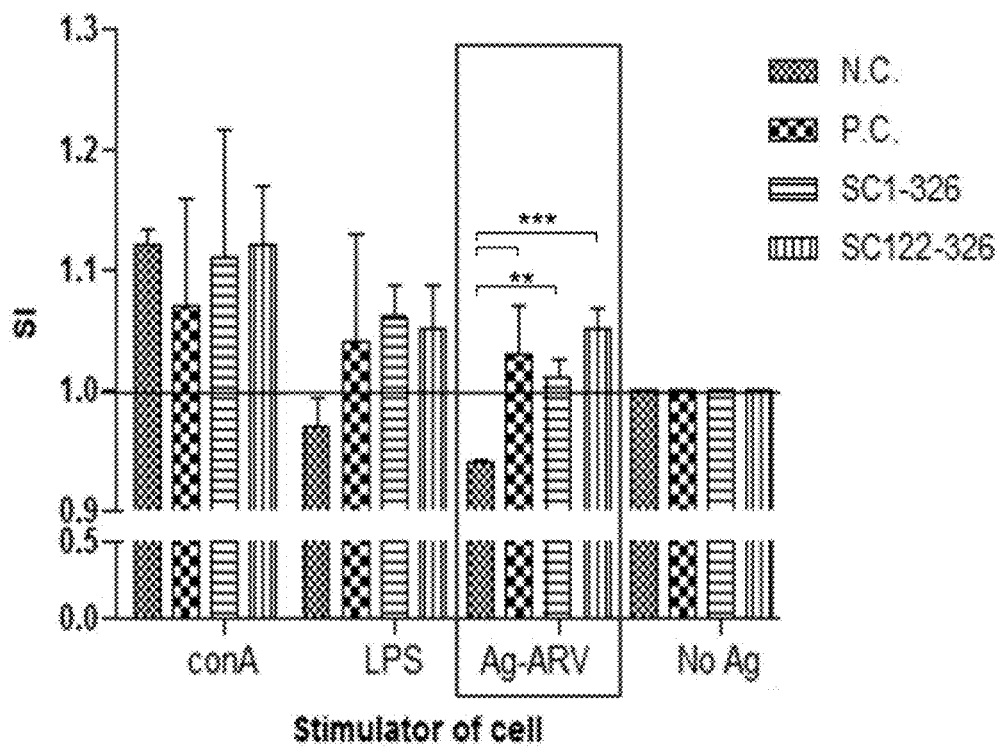
FIG. 4 depicts a bar graph showing proliferation of lymphocytes derived from spleens of birds vaccinated with PBS in adjuvant as negative control (N.C.), ARV vaccine strain s1133 as positive control (P.C.), SC1-326 or SC122-326, following stimulation with ARV. Cells were treated with concanavalin A (ConA) or lipopolysaccharide (LPS) as controls for nonspecific antigen (Ag) cell proliferation, ARV for specific Ag proliferation, or the medium itself as a negative control (N.C.). The measured absorbance is proportional to the number of viable cells. Results are presented as stimulation index (SI) representing the ratio between stimulated and non-stimulated cells. *, Significantly different at P<0.001 and 0.01, respectively.

Three different fragments of the protein—residues 1-326, 122-326, and 192-326 (FIG. 5)—were identified and tested in accordance with the present invention as candidates for subunit vaccine that will elicit the highest levels of anti-ARV neutralizing antibodies. The present invention is based on the finding that while SC1-326 induces low titer of antibodies, the other two fragments induced an immune response with high antibody titers, the most prominent one being SC122-326 (FIG. 2). It was further found that following stimulating of splenocytes isolated from birds vaccinated with different SC polypeptides, only cells from birds that were exposed to SC122-326 polypeptide proliferated to the same extent as the positive control, which was vaccinated with the whole virus (FIG. 4).

Figure 5:
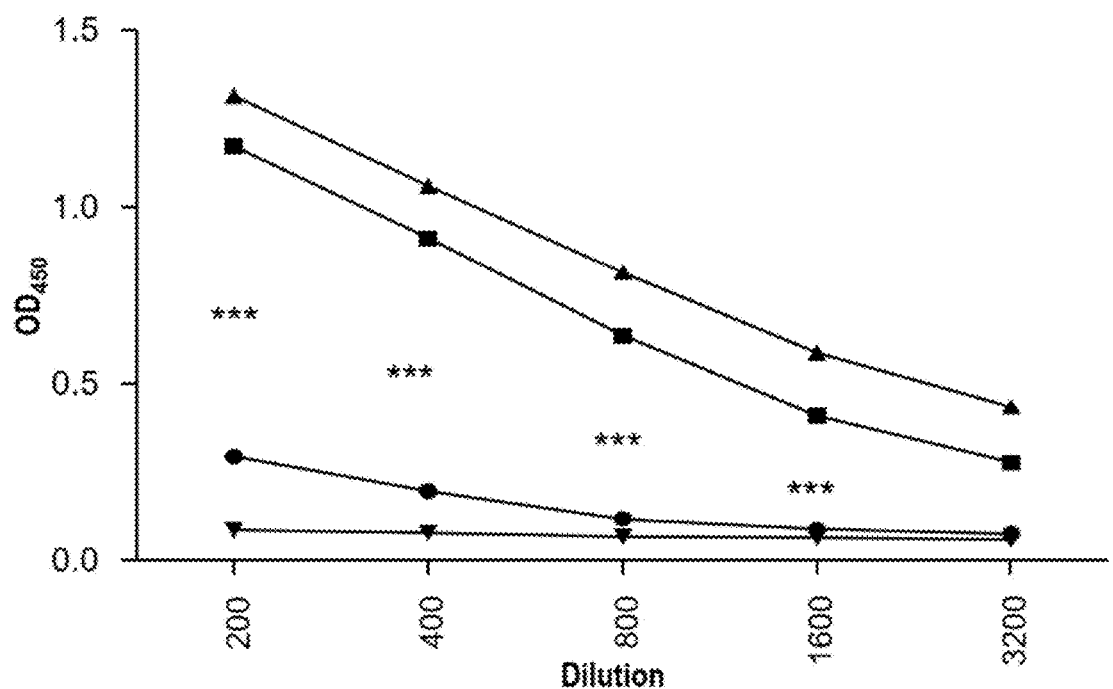
FIG. 5 depicts a line graph showing the effect of primary vaccination with SC122-326 on the secondary response to ARV. Results are expressed as dilution end-points, tested by ELISA (optical density (OD) measured at 450 nm). Negative control-vaccinated with PBS and adjuvant. Circles—Primary immune response to ARV vaccine strain s1133; Squares—Immune response to ARV after primary vaccination with SC122-326; Upright triangles—Immune response to ARV after primary vaccination with ARV; —Inverted triangles—Negative control. ***Significantly different at P<0.001.

As SC122-326 yielded the highest levels of antibodies, it was further analyzed. The ability to get a secondary immune response against ARV following priming with SC122-326 indicated that the same B and T lymphocytes are induced by SC122-326 and the whole virus (FIG. 5). This enables vaccinating at a young age with SC122-326 and overcomes the disruption of maternal antibodies in eliciting a full response.

The efficacy of SC122-326 as a vaccine against ARV was further tested by viral neutralization test. Antibodies produced against the SC protein showed successful neutralization in cell systems [28,45]. However, neutralization tests are more accurate at predicting viral neutralization in adult birds. It has thus been found in accordance with the present invention that antibodies produced following injection of SC122-326 protein are protective, eliminating infection of bird embryos by the virulent strain to the same extent as antibodies produced in response to the whole virus (Table 5). It is noteworthy that antibodies produced following injection of the whole SC protein (SC1-326) are not protective. It is thus self-evident that the isolated polypeptide SC122-326 has markedly different characteristics than the counterpart within the context of the whole protein.

Figure 6:
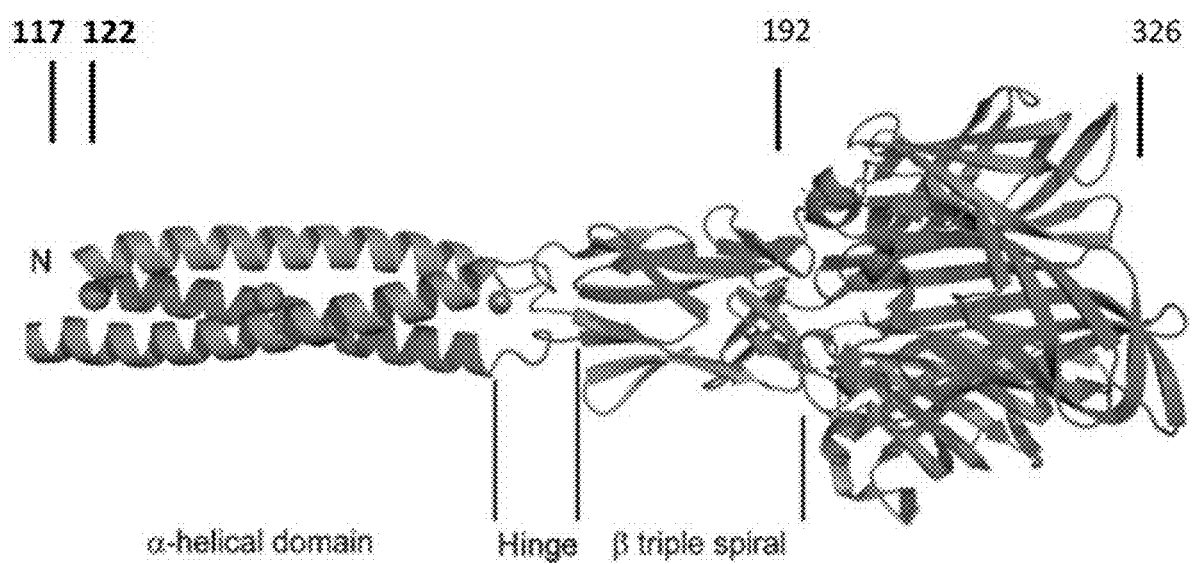
FIG. 6 depicts a model of a partial structure (amino acids 117-326) of sigma C (SC) protein of avian reovirus strain s1133. Numbers represent amino acid positions in the protein structure. Adopted from Guardado-Calvo et al. [18].

In view of the above, in one aspect, the present invention is directed to an isolated polypeptide comprising, or essentially consisting of, an amino acid sequence corresponding to the amino acid residues forming a full or partial α-helical domain, the hinge domain, the β-triple spiral domain and a full or partial globular head domain of an avian reovirus sigma C protein as depicted in FIG. 6, and lacking the amino acid sequence that is N-terminal to said α-helical domain.

The term "isolated polypeptide" refers to the fact that the amino acid sequence is a fragment of the full-length sigma c protein, which is expressed outside its natural context within the full-length sigma c protein, and is used interchangeably herein with the terms "recombinant polypeptide", "synthetic polypeptide" or "fragment of full-length sigma c protein".

The different domains of the sigma C protein are well characterized as taught in Guardado-Calvo, 2009; When the overall structure is contemplated, a clear division between shaft (amino acid residues 117-191) and globular head domains (amino acid residues 196-326) is observed. The shaft domain can be further subdivided into an α-helical triple coiled-coil (amino acid residues 117-154), a linker region (amino acid residues 155-159) and two repeats of a triple β-spiral (amino acid residues 160-191).

In certain embodiments, the isolated polypeptide comprises, or essentially consists of, an amino acid sequence corresponding to amino acid residues 70-326, 117-326, or particularly 122-326, of the sigma C protein of the ARV strain S1133 as set forth in SEQ ID NO: 1, referred to herein as "the internal protein sequence of S1133" or "the internal amino acid sequence". In particular, the internal amino acid sequence has at least 40%, at least 50%, at least 60%, at least 70%, at least 80%, at least 85%, at least 90%, or at least 95, 96, 97, 98, or 99% identity to the amino acid sequence corresponding to amino acid residues 70-326, 117-326, or 122-326 of the sigma C protein of the ARV strain S1133 as set forth in SEQ ID NO: 1.

In further particular embodiments, any one of the isolated polypeptides defined above blocks or reduces the binding of infectious avian reovirus to the native receptor of sigma C protein of an avian reovirus. Methods for measuring binding of ligands to proteins are well known in the art, for example, by surface plasmon resonance (SPR) as described in Barton Erik S, J. Craig Forres, Jodi L Connolly, James D Chappell, Yuan Liu, Frederick J Schnell, Asma Nusrat, Charles A Parkos, Terence S Dermody. Junction Adhesion Molecule Is a Receptor for Reovirus. Cell, Vol. 104, 441-451, Feb. 9, 2001.

In even more particular embodiments, any one of the isolated polypeptides defined above, when administered to a bird, optionally in combination with an adjuvant, induces a protective immune response against an infectious avian reovirus. In certain embodiments, when any one of the isolated polypeptides defined above is administered to a bird, it induces the production of significantly higher systemic levels of neutralizing anti-sigma C protein antibody as compared with the systemic levels of said antibody obtained after administration to a bird of full length sigma C protein of the ARV strain S1133. Methods for measuring induction of protective immune response in birds are well known in the art. For example, as taught in the Examples below, the antibody titer can easily be measured in the serum of vaccinated birds by ELISA test and the ability of the sera to neutralize virulent reovirus can easily be done by monitoring inhibition of embryonic mortality after inoculation with a live virus.

In certain embodiments, any one of the isolated polypeptides defined above comprises an amino acid sequence having at least 40%, at least 50%, at least 60%, at least 70%, at least 80%, at least 85%, at least 90%, or at least 95, 96, 97, 98, or 99% identity to the internal amino acid sequence of a sigma C protein selected from the group disclosed in Table 1, said internal amino acid sequence corresponding to amino acid residues 70-326, 117-326 or 122-326 of the sigma C protein of the ARV strain S1133 as set forth in SEQ ID NO: 1.

In certain embodiments, any one of the isolated polypeptides defined above comprises an amino acid sequence corresponding to an internal amino acid sequence within the amino acid sequence of a sigma C protein selected from the group disclosed in Table 1, said internal amino acid sequence corresponding to amino acid residues 70-326, 117-326 or 122-326 of the sigma C protein of the ARV strain S1133 as set forth in SEQ ID NO: 1.

In particular embodiments, the isolated polypeptide comprises, or essentially consists of, an amino acid sequence selected from the group consisting of SEQ ID NO: 2, SEQ ID NO: 3, SEQ ID NO: 4 and SEQ ID NO: 5, such as SEQ ID NO: 2 (i.e. internal protein sequence of S1133, ISR5223, ISR5215 and ISR528, respectively).

TABLE 1

Database accession numbers for representative full length avian reovirus sigma c proteins.

| Isolate | Accession numbers[1] | SIN[2] |
|---------|---------------------|--------|
| S1133 | AAK18188.1 | 1 |
| ISR521 | FJ793522 | 6 |
| ISR526 | FJ793537 | 7 |
| ISR5215 | FJ793531 | 8 |
| ISR5220 | FJ793532 | 9 |
| ISR5225 | FJ793546 | 10 |
| ISR5226 | FJ793547 | 11 |
| ISR522 | FJ793540 | 12 |
| ISR5217 | FJ793535 | 13 |
| ISR5221 | FJ793542 | 14 |
| ISR5222 | FJ793543 | 15 |
| ISR5223 | FJ793544 | 16 |
| ISR524 | FJ793525 | 17 |
| ISR527 | FJ793529 | 18 |

TABLE 1-continued

Database accession numbers for representative full length avian reovirus sigma c proteins.

| Isolate | Accession numbers[1] | SIN[2] |
|---------|---------------------|--------|
| ISR528 | FJ793523 | 19 |
| ISR529 | FJ793528 | 20 |
| ISR5211 | FJ793524 | 21 |
| ISR5213 | FJ793533 | 22 |
| 59103 | AAQ01229.1 | 23 |
| ISR5212 | FJ793526 | 24 |
| ISR5210 | FJ793527 | 25 |
| ISR5216 | FJ793530 | 26 |
| ISR5234 | FJ793534 | 27 |
| ISR5231 | FJ793536 | 28 |
| ISR5229 | FJ793538 | 29 |
| ISR525 | FJ793539 | 30 |
| ISR523 | FJ793541 | 31 |
| ISR5224 | FJ793545 | 32 |
| ISR5219 | FJ793548 | 33 |
| ISR5233 | FJ793549 | 34 |

[1]NCBI database at http://www.ncbi.nlm.nih.gov;
[2]SIN, SEQ ID NO:

In certain embodiments any one of the isolated polypeptides defined above further comprises a tag for identification and/or purification, such as a polyhistidine tag, (e.g. His$_6$), but it may also be a (His-Asn)$_6$ tag, a Flag tag, or any other tag that may facilitate the purification of the polypeptide. A sole tag or multiple copies of it can be used or different tags can be used in combination. The tag(s) can be fused to the C-terminus or the N-terminus of the polypeptide. For example, the isolated polypeptide having an internal amino acid sequence in a protein set forth in any one of SEQ ID Nos: 1 and 6-34, such as SEQ ID NO: 2, SEQ ID NO: 3, SEQ ID NO: 4 or SEQ ID NO: 5, may further comprises a tag for identification and/or purification, such as those described above.

For expression of the polypeptides described above, bacterial or eukaryotic cells, such as yeast or plant cells, may be transformed with the nucleic acid molecule and the expressed polypeptide may be purified using the purification tag inserted into the polypeptide and/or by other protein purification methods well known in the art. Preferably, the polypeptide is expressed in a bacterial cell, more preferably E. coli.

For use in immunogenic compositions/vaccines, any one of the polypeptides defined above may be combined with a carrier protein such as, but not limited to, E. coli heat labile enterotoxin (LT), bovine serum albumin and flagellin. The carrier protein may be fused to the N- or the C terminus of the polypeptide or it may flank the polypeptide on both ends. The carrier protein may be fused to the polypeptide by recombinant techniques, i.e. the polypeptide and the carrier protein are encoded by a single nucleic acid sequence and are expressed as a continuous polypeptide. Alternatively, the polypeptide and the carrier protein may be produced separately and then chemically attached to each other.

The preferred carrier protein for all aspects of the present invention is the LT protein. It confers the function of carrier and is also known as a powerful adjuvant in injection and oral administration that is capable of eliciting strong systemic IgG and local IgA responses as well as cytotoxic helper T-cell response. Since the reovirus is a mucosal antigen, it is preferential to stimulate the immune response of the mucosal system. IgA antibodies developed by oral vaccinations in mucosal tissues are the main deterrents against the challenge offered by mucosal antigens. The LT protein is a hexamer that consists of two subunits: the 27-kDa catalytic A domain (LTA) anchored in a ring of five identical 11.6-kDa B subunits (LTBs). The A1 fragment is toxic and catalyzes the transfer of an ADP-ribose from NAD to stimulatory α-subunits of G proteins (Gsα). To use LT as an immunostimulator in animals, its toxicity may be neutralized by mutations (Vasserman, Y. and Pitcovski, J., 2006). Either one of the A and B subunits may be used in conjunction with the polypeptide of the invention.

The polypeptide may also be attached to physiologically acceptable microbeads, which may carry enhancer molecules such as LT in addition to the polypeptide. Alternatively, the polypeptide may be bound indirectly to the carrier via antibodies or biotinylated polypeptides may be bound to the carrier via avidin or streptavidin.

Microparticles intended for use in the present invention preferably have a size in the range from 10 nm to 200 µm. The size chosen for a particular microparticle will depend on the active agent to be delivered, and the intended route of administration. For oral delivery, particles are conveniently in the size range 0.5 to 5.0 µm. For subcutaneous delivery, a suitable size is less than 100 µm. Microparticles for parenteral delivery conveniently have a size of less than 200 µm, preferably less than 150 µm.

In an additional aspect, the present invention provides a nucleic acid molecule comprising a nucleic acid sequence encoding at least one of the isolated polypeptides defined above.

In another aspect, the present invention provides an expression vector comprising a control element, such as a promoter, operably linked to the nucleic acid molecule defined above, wherein said expression vector is designed to replicate and express relevant genes in for example a bacterial, yeast or insect cell.

The invention further contemplates cells comprising and/or expressing any one of the expression vectors defined above. Examples of cells suitable for expressing the polypeptides of the present invention are bacterial cells, such as E. coli, yeast cells, insect cells, plant cells or mammalian cells.

In a further aspect, the present invention provides a vaccine comprising at least one of the isolated polypeptides defined above.

In still a further aspect, the present invention provides a vaccine comprising a mammalian expression vector, such as pcDNA3, comprising a control element, such as a promoter, operably linked to any one of the nucleic acid molecules defined above.

In yet an additional aspect, the present invention provides a viral vector, such as a recombinant Marek's disease (MD) virus, comprising a control element, such as a promoter, operably linked to any one of the nucleic acid molecules defined above.

WO 2009/093251, incorporated by reference as if fully disclosed herein, discloses that the highly variable and immunogenic avian reovirus sigma C protein amino acid sequence contains conserved and immunogenic domains that are common among all avian reovirus isolates identified in Israel and elsewhere. The identified conserved sequences are located between amino acid residue corresponding to amino acid residues 170 and 323 of the sigma C protein of the ARV strain S1133 as set forth in SEQ ID NO: 1.

The term "conserved domain" refers herein to a domain conserved among the virus variants; namely, the amino acid sequences of the domains are similar but not necessarily absolutely identical to each other.

WO 2009/093251 further discloses that the genetically variable avian reovirus strains, or isolates, infecting birds in Israel and elsewhere can be divided into four groups according to the variability in the amino acid sequence of the sigma C protein expressed by the isolates. One member of one of the groups represents only a fraction of the avian reovirus isolates in nature; however, one member of each of the four groups taken together represent many, if not most, variants existing in nature. The four groups of reovirus isolates (RI) are referred to herein as RI Groups I to IV (Table 2).

The defining feature of each RI group is that the amino acid sequences of the different sigma c proteins of said RI group has at least 75% identity. The composition of the groups may vary slightly depending on the algorithm and software used to analyze the sequences. The important concept is that each group represents a fraction of the viral population and that single representatives taken from each one of the groups together represent the whole viral population.

Since the conserved immunogenic domains are found within the isolated polypeptide of the present invention, the concept disclosed in WO 2009/093251 can be used to produce an improved vaccine comprising isolated polypeptides of the present invention that represents the whole viral population.

It has been found in accordance with the present invention that the internal polypeptide of sigma c proteins of four different avian reovirus variants, each one of which corresponds to amino acid residues 122-326 of the sigma C protein of the ARV strain S1133 as set forth in SEQ ID NO: 1 can be effectively expressed in vitro.

In certain embodiments, the vaccine comprises at least two different recombinant polypeptides; or in the case of the vaccine comprising a mammalian expression vector or the viral vector, the nucleic acid molecule encodes at least two different recombinant polypeptides; and each one of said at least two different recombinant polypeptides is derived from a representative of one of two, three or four groups of different sigma c proteins, wherein the defining feature of each group is that the amino acid sequences of the different sigma c proteins of said group has at least 75% identity, optionally as defined in Table 2 and as taught in WO 2009/093251, incorporated by reference as if fully disclosed herein. The term "derived from" as used herein means that the recombinant polypeptide is a fragment of the representative sigma c protein comprising an amino acid sequence corresponding to amino acid residues 70-326, 117-326 or 122-326 of the sigma C protein of the ARV strain S1133 as set forth in SEQ ID NO: 1. The vaccine may be modified by replacing one polypeptide that is a representative for one group with another polypeptide from the same group.

TABLE 2

Reovirus Isolates (RI) from Israel arranged in four RI groups and SEQ ID NO (SIN) of sigma C proteins (SCP) arranged in four corresponding SCP groups.

| RI # | SCP SIN[2] |
|---|---|
| I | |
| ISR521 | 6 |
| ISR526 | 7 |
| ISR5215[1] | 8 |
| SR5220 | 9 |
| ISR5225 | 10 |
| ISR5226 | 11 |

TABLE 2-continued

Reovirus Isolates (RI) from Israel arranged in four RI groups and SEQ ID NO (SIN) of sigma C proteins (SCP) arranged in four corresponding SCP groups.

| RI # | SCP SIN[2] |
|---|---|
| II | |
| ISR522 | 12 |
| ISR5217 | 13 |
| ISR5221 | 14 |
| ISR5222 | 15 |
| ISR5223 | 16 |
| III | |
| ISR524 | 17 |
| ISR527 | 18 |
| ISR528 | 19 |
| ISR529 | 20 |
| ISR5211 | 21 |
| ISR5213 | 22 |
| IV | |
| 59103 | 23 |
| S1133 | 1 |

[1]bold: isolates expressing the sigma C protein variant most identical to its group.
[2]SIN, SEQ ID NO:

For example, one of the at least two different isolated polypeptides may be an isolated polypeptide derived from a sigma c protein that has at least 75% identity to SEQ ID NO: 6-11 (Group I); a polypeptide derived from a sigma c protein that has at least 75% identity to SEQ ID NOs: 12-16 (Group II); a polypeptide derived from a sigma c protein that has at least 75% identity to SEQ ID NOs: 17-22 (Group III); or a polypeptide derived from a sigma c protein that has at least 75% identity to SEQ ID NOs: 1 and 23 (Group IV). The vaccine further includes one, two, three or more additional different polypeptides as defined above. In particular embodiments, in each one of the above relevant combinations, the different polypeptides have an amino acid sequence as set forth in SEQ ID NO: 2, SEQ ID NO: 3, SEQ ID NO: 4 or SEQ ID NO: 5.

In another example, two of the at least two different polypeptides may be a first polypeptide derived from a sigma c protein that has at least 75% identity to SEQ ID NOs: 6-11 (Group I) and a second polypeptide derived from a sigma c protein that has at least 75% identity to SEQ ID NOs: 12-16 (Group II); a first polypeptide derived from a sigma c protein that has at least 75% identity to SEQ ID NOs: 6-11 (Group I) and a second polypeptide derived from a sigma c protein that has at least 75% identity to SEQ ID NOs: 17-22 (Group III); a first polypeptide derived from a sigma c protein that has at least 75% identity to SEQ ID NO: 6-11 (Group I) and a second polypeptide derived from a sigma c protein that has at least 75% identity to SEQ ID NOs: 1 and 23 (Group IV); a first polypeptide derived from a sigma c protein that has at least 75% identity to SEQ ID NO: 12-16 (Group II) and second polypeptide derived from a sigma c protein that has at least 75% identity to SEQ ID NOs: 17-22 (Group III); a first polypeptide derived from a sigma c protein that has at least 75% identity to SEQ ID NOs: 12-16 (Group II) and second polypeptide derived from a sigma c protein that has at least 75% identity to SEQ ID NOs: 1 and 23 (Group IV); or a first polypeptide derived from a sigma c protein that has at least 75% identity to SEQ ID NOs: 17-22 (Group III) and second polypeptide derived from a sigma c protein that has at least 75% identity to SEQ ID NOs: 1 and 23 (Group IV). The vaccine further includes one, two or more additional different polypeptides as defined above.

In particular embodiments, in each one of the above relevant combinations, the two different polypeptides have an amino acid sequence as set forth in SEQ ID NO: 2, SEQ ID NO: 3, SEQ ID NO: 4 or SEQ ID NO: 5.

Alternatively, three of the at least two different polypeptides may be a first polypeptide derived from a sigma c protein that has at least 75% identity to SEQ ID NOs: 6-11 (Group I), a second polypeptide derived from a sigma c protein that has at least 75% identity to SEQ ID NOs: 12-16 (Group II) and a third polypeptide derived from a sigma c protein that has at least 75% identity to SEQ ID NOs: 17-22 (Group III); a first polypeptide derived from a sigma c protein that has at least 75% identity to SEQ ID NOs: 6-11 (Group I), a second polypeptide derived from a sigma c protein that has at least 75% identity to SEQ ID NOs: 12-16 (Group II) and a third polypeptide derived from a sigma c protein that has at least 75% identity to SEQ ID NOs: 1 and 23 (Group IV); a first polypeptide derived from a sigma c protein that has at least 75% identity to SEQ ID NOs: 6-11 (Group I), a second polypeptide derived from a sigma c protein that has at least 75% identity to SEQ ID NOs: 17-22 (Group III) and a third polypeptide derived from a sigma c protein that has at least 75% identity to SEQ ID NOs: 1 and 23 (Group IV); or a first polypeptide derived from a sigma c protein that has at least 75% identity to SEQ ID NOs: 12-16 (Group II), a second polypeptide derived from a sigma c protein that has at least 75% identity to SEQ ID NOs: 17-22 (Group III) and a third polypeptide derived from a sigma c protein that has at least 75% identity to SEQ ID NOs: 1 and 23 (Group IV). In particular embodiments, in each one of the above relevant combinations, the three different polypeptides have an amino acid sequence as set forth in SEQ ID NO: 2, SEQ ID NO: 3, SEQ ID NO: 4 or SEQ ID NO: 5. The vaccine further includes one or more additional different polypeptides as defined above.

In certain embodiments, the vaccine comprises four different polypeptides; or the vaccine comprising mammalian expression vector or the viral vector comprises a nucleic acid molecule encoding four different polypeptides, wherein the first of said four different polypeptides is derived from a sigma c protein that has at least 75% identity to SEQ ID NOs: 6-11 (Group I); the second of said four different polypeptides is derived from a sigma c protein that has at least 75% identity to SEQ ID NOs: 12-16 (Group II); the third of said four different polypeptides is derived from a sigma c protein that has at least 75% identity to SEQ ID NOs: 17-22 (Group III); and the fourth of said four different polypeptides is derived from a sigma c protein that has at least 75% identity to SEQ ID NO: 1 or 23 (Group IV).

In particular embodiments, the first of said four different polypeptides is derived from a sigma c protein that has at least 40%, at least 50%, at least 60%, at least 70%, at least 80%, at least 85%, at least 90%, or at least 95, 96, 97, 98, or 99% identity to SEQ ID NO: 8 (Group I); the second of said four different polypeptides is derived from a sigma c protein that has at least 40%, at least 50%, at least 60%, at least 70%, at least 80%, at least 85%, at least 90%, or at least 95, 96, 97, 98, or 99% identity to SEQ ID NO: 16 (Group II); the third of said four different polypeptides is derived from a sigma c protein that has at least 40%, at least 50%, at least 60%, at least 70%, at least 80%, at least 85%, at least 90%, or at least 95, 96, 97, 98, or 99% identity to SEQ ID NO: 19 (Group III); and the fourth of said four different polypeptides is derived from a sigma c protein that has at least 40%, at least 50%, at least 60%, at least 70%, at least 80%, at least 85%, at least 90%, or at least 95, 96, 97, 98, or 99% identity to SEQ ID NO: 23 (Group IV).

In particular embodiments, the first of said four different polypeptides is derived from a polypeptide selected from the group consisting of SEQ ID NO: 6-11 (Group I); the second of said four different polypeptides is derived from a polypeptide selected from the group consisting of SEQ ID NO: 12-16 (Group II); the third of said four different polypeptides is derived from a polypeptide selected from the group consisting of SEQ ID NO: 17-22 (Group III); and the fourth of said four different polypeptides is derived from a polypeptide selected from the group consisting of SEQ ID NO: 1 and 23 (Group IV). In more particular embodiments, the four different polypeptides have an amino acid sequence as set forth in SEQ ID NO: 2, SEQ ID NO: 3, SEQ ID NO: 4 and SEQ ID NO: 5.

In certain embodiments, any one of the vaccines of the present invention comprises a pharmaceutically acceptable amount of a pharmaceutically acceptable diluent or carrier. Pharmacologically acceptable diluents and carriers suitable for use in the vaccine of the invention may be any conventional liquid carrier suitable for veterinary pharmaceutical compositions, such as a balanced salt solution suitable for use in tissue or cell culture media, e.g. sterile phosphate buffered saline or distilled water. Other suitable media can include emulsions. Non-fat dry milk may be utilized as a carrier in vaccines formulated for application via drinking water.

In certain embodiments, any one of the vaccines of the present invention, whether it comprises a pharmaceutically acceptable amount of a pharmaceutically acceptable diluent or carrier or not, further comprises an adjuvant, such as heat-labile enterotoxin (LT), complete Freund adjuvant, incomplete Freund adjuvant, aluminium hydroxide; and/or a preservative, such as thimerosal or 20% water-in-oil emulsions with for example Marcol 52 mineral oil (ESSO, France).

In yet another aspect, the present invention is directed to any one of the vaccines or viral vectors defined above, for use in vaccination of an avian species or for use in inducing an avian immune response conferring protection against avian reovirus. The vaccine or viral vector may be used along with a pharmaceutically acceptable amount of a pharmaceutically acceptable diluent or carrier and/or an adjuvant as described above.

In yet an additional aspect, the present invention is directed to a method for vaccinating an avian species or for inducing an avian immune response conferring protection against avian reovirus, which comprises administering any one of the vaccines or viral vectors defined above to a bird. In particular embodiments, the vaccine comprises a combination of four isolated polypeptides as described above. The vaccine or viral vector may be administered along with a pharmaceutically acceptable amount of a pharmaceutically acceptable diluent or carrier and/or an adjuvant as described above.

In certain embodiments, the avian species that can be vaccinated using any one of the vaccines and methods described herein is any bird species which is produced commercially, such as poultry, e.g. chickens, turkeys, ducks, geese, pheasants, pigeons or guinea fowl.

In certain embodiments, the use or method disclosed above induces the production of significantly higher, for example statistically significantly higher, systemic levels of neutralizing anti-sigma C protein antibody as compared with the systemic levels of said antibody obtained after administration to said bird of full length sigma C protein of the ARV strain S1133.

In certain embodiments the vaccine may be administered by any suitable route of administration such as by injection, intradermally or subcutaneously; or orally via the drinking water.

The invention will now be illustrated by the following non-limiting examples.

EXAMPLES

Materials and Methods

Expression of the SC Protein

Three cDNA fragments of SC from the vaccine strain s1133 encoding SC residues 1-326, 122-326 and 192-326 were produced by polymerase chain reaction (PCR) with specifically designed oligonucleotides (Table 3). Fragments 122-326 and 192-326 were cleaved with restriction enzymes BamHI and EagI introduced into the primers during synthesis, and were

TABLE 3

Designed oligonucleotides for amplification of sigma C (SC) fragments.

| Label[a] | Direction | Primer sequences (5'→3') | Expected size (bp) |
| --- | --- | --- | --- |
| SC122-326 | Forward | GGGGGATCCGACGGAAACTCCACTGCC | 669 |
| SC122-326 | Reverse | GGGCGGCCGTTAGGTGTCGATGCCGG | |
| SC192-326 | Forward | GGGGGATCCTCGGCGGAGGCTCAACTAATGC | 459 |
| SC192-326 | Reverse | GGGCGGCCGTTAGGTGTCGATGCCGG | |

[a]Oligonucleotides were designed to amplify the gene encoding SC122-326 and SC192-326 partial proteins; the 5' ends of the oligonucleotides were designed to create restriction enzyme sites BamHI-EagI, BamHI-EagI, and EcoRI-EcoRI (underlined), respectively, after PCR amplification.

cloned into the expression vector pET28a (Novagen, Darmstadt, Germany), which included a purification tag containing six consecutive histidine residues at the N terminus. The sequence of the insert was confirmed by DNA-sequence analysis (Hy-Labs, Rehovot, Israel). For expression, *Escherichia coli* strain BL21 (DE3) was freshly transformed with the plasmid. Cultures were grown aerobically at 37° C. to an optical density (OD) at 600 nm of 0.6-0.8. The cultures were cooled to below 25° C., and expression was induced by adding 1 mM isopropyl β-D-1-thiogalactopyranoside (IPTG) and incubating for 3 h at 25° C. Harvested cells were resuspended in 40 ml cold resuspension buffer (4.29 mM $Na_2HPO_4$, 1.47 mM $KH_2PO_4$, 2.7 mM KCl, 137 mM NaCl, 0.1% v/v Tween-20) and frozen at −20° C. (Guardado-Calvo et al. 2009). Bacteria were lysed by sonicating three times for 10 min each time (Sonics, Taunton, Mass., USA), centrifuged (10,000×g for 15 min at 4° C.) and the pellet was discarded. SC residue 1-326 was expressed as described previously (Goldenberg et al. 2011). The expressed SC122-326 protein fragment was purified in a Ni-NTA agarose column according to the manufacturer's instructions (Qiagen, Hilden, Germany). The purified protein was dialyzed overnight against phosphate buffered saline (PBS) at 4° C. The expressed SC proteins were detected by 12% SDS-polyacrylamide gel electrophoresis (PAGE). The amount of SC protein was estimated by comparison with a standard curve of known amounts of bovine serum albumin run on the same gel.

Cloning and Expression of SC in *Pichia Pastoris*

A DNA fragment encoding SC residues 1-326 was produced by PCR with specifically designed oligonucleotides (Table 3). This fragment was cleaved by the restriction enzyme EcoRI (GAATTC), which was introduced by the primers during synthesis. The isolated fragment was ligated to plasmid pHILD2 provided in the *P. pastoris* kit (Invitrogen, San Diego, Calif., USA) as described previously (Pitcovski et al. 2003). Briefly, the ligated DNA construct was transformed into *E. coli* XL1-blue cells and white colonies that grew on LB (luria-bertani) plates containing ampicillin (100 g/ml), X-Gal to final concentration of 80 μg/ml and IPTG to final concentration of 20 mM were isolated. Following characterization, a plasmid harboring SC with the correct sequence was cloned into *P. pastoris* as follows.

The vector was linearized and introduced into *P. pastoris* cells, resulting in the insertion of the transgene at the AOX1 locus. Positive colonies were grown and recombinant protein production was induced by adding methanol. Following induction, cells were lysed by vortexing with glass beads, centrifuged, and the supernatant containing the soluble SC was analyzed by SDS-PAGE.

Enzyme-Linked Immunosorbent Assay (ELISA)

To determine the anti-SC antibody titer, SC was used as the antigen in an ELISA. The antigen was diluted in coating buffer (0.397 g $Na_2CO_3$, 0.732 g $NaHCO_3$, 250 ml double-distilled water pH 9.6) and incubated in an ELISA plate (Nunc, Rochester, N.Y., USA) for 24 h at 4° C. Each subsequent step was followed by three washes with 0.05% Tween-20 in PBS. Serum from birds vaccinated with the tested proteins or controls were serially double-diluted (1:100-1:800,000) in a blocking buffer (5% w/v skim milk, 0.05% Tween-20 in PBS) and incubated for 1 h. The secondary antibody, peroxidase-conjugated rabbit anti-chicken IgG (Sigma, Rehovot, Israel), diluted 1:7000, was added and the mixture was incubated for 1 h. The substrate o-phenylenediamine dihydrochloride (Sigma) was then added. OD was measured by ELISA reader (Thermo Scientific Multiskan RC, Vantaa, Finland) at 450 nm. The end-point titer was determined as the last dilution for which the OD was still positive (relative to the negative control in the ELISA).

The level of anti-ARV antibodies in the sera of vaccinated birds was determined by a commercial ELISA (IDEXX® Laboratories, USA) according to the manufacturer's instructions. OD values were measured at 650 nm. Sample-to-positive (S/P) ratios greater than 0.2 were considered to be positive for ARV (S/P ratio=sample mean OD)−negative control mean OD/positive control mean OD−negative control mean OD).

Cell Proliferation Assay

Spleens were collected from birds 42 days post-vaccination and macerated with a syringe plunger through a screen sieve to obtain a single-cell suspension in PBS. Splenocytes were suspended in RPMI 1640 supplemented with 2% fetal bovine serum, 2 mM L-glutamine, penicillin (100 U/ml) and streptomycin (10 ng/ml) (Biotech Industry, Bet Haemek, Isarel). Cells ($1 \times 10^6$ per well) were seeded in 96-well culture plates. Concanavalin A (ConA; 5 μg/ml), lipopolysaccharide (LPS; 5 μg/ml) or ARV (5 μl/well, at a titer of $10^{6.6}$) (Sigma Aldrich) were added as stimulators in triplicate and incubated for 48 h. Cell titer blue (CTB) assay was performed by adding 20 μl CTB reagent (Promega, Madison, Wis., USA) to each well. The cells were then incubated for 6 h at 37° C. under 5% $CO_2$. Color intensity of the CTB reagent was quantified by fluorometer at excitation/emission wavelengths of 560 and 590 nm, respectively. The measured absorbance was proportional to the number of viable cells. Results were calculated and presented as stimulation index (SI), representing the ratio between stimulated cells and non-stimulated cells.

Neutralization Test of Virulent ARV Strain s1133

The ability of the sera to neutralize virulent reovirus was tested by monitoring inhibition of embryonic mortality 3-7 days post-inoculation. The tested sera were filtered and heated for 30 min at 56° C. to inactivate complement activity. The virus was diluted with PBS in a series of 10-fold dilutions. Mixtures of equal volumes of diluted virus and sera (or PBS as a negative control) were incubated for 40 min at room temperature. Each of the mixtures was inoculated into five fertile 7-day-old SPF embryonated eggs.

To confirm the virulence potential of the indicator virus, 10 eggs were inoculated with the undiluted virus that was mixed 1:1 with PBS. In addition, in several of the experiments, virus-free sera were inoculated into embryonated eggs to confirm the absence of nonspecific mortality due to serum constituents. All eggs were illuminated daily in a dark room to determine embryo viability, and the number of live and dead embryos was recorded.

The neutralization index (NI) was determined as the ratio between the highest virus dilution that killed at least 95% (cumulative) of the embryos and the virus dilution that killed the same percentage of embryos in the presence of antibodies. NI value was expressed as the ratio between the log of the dilutions. A NI of 2 or greater in the antiserum was considered as having neutralized the virus.

TABLE 4

| Vaccination program. | | |
|---|---|---|
| Group | Vaccine at 14 d[a] | Vaccine at 28 d[a] |
| 1 | ARV s1133[b] | ARV s1133 |
| 2 | PBS+adjuvant[c] | PBS+adjuvant |
| 3 | SC1-326 | SC1-326 |
| 4 | SC122-326 | SC122-326 |
| 5 | SC192-326 | SC192-326 |
| 6 | SC122-326 | ARV s1133 |

[a]Days of age;
[b]Positive control;
[c]Negative control.

Statistics

ELISA, neutralization and cell-proliferation results were analyzed by one-way analysis of variance (ANOVA) with Tukey test. All of the analyses were performed with GraphPadPrism5 software.

Example 1

SC Protein Expression

Following analysis of the SC protein structure, cDNA fragments encoding three polypeptides residues: 1-326, 122-

326, 192-326, were produced, cloned, and expressed in *E. coli*. A polyhistidine tag was added at the 5' end to allow for detection and purification of the expressed proteins. The resultant proteins were partially purified. The expressed SC fragments were at expected sizes of 36 kD, 23 kD and 15kD (respectively) as determined on a 12% SDS-polyacrylamide gel.

Figure 1A:
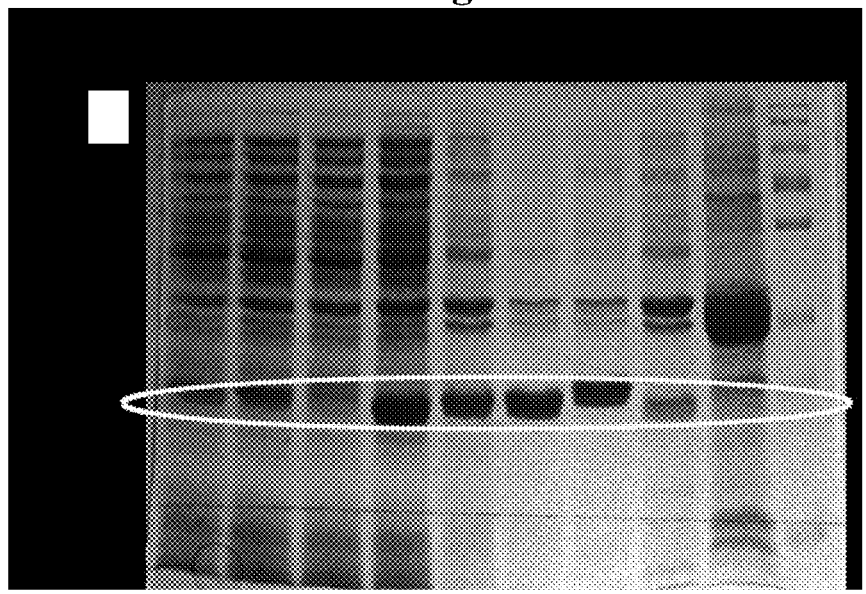
FIGS. 1A-B show efficient expression of Sigma C of ARV isolates; His-tagged residues 122-326 was expressed in *E. coli* BL21. Coomassie Brilliant Blue staining (A) show robust expression of proteins of the expected molecular size. Their identity was confirmed using mouse anti-His monoclonal antibody via western blot (B). Lane 1: soluble SC1133, Lane 2: soluble SC528, Lane 3: soluble SC5223, Lane 4: soluble SC5215, Lane 5: insoluble SC1133, Lane 6: insoluble SC528, Lane 7: insoluble SC5223, Lane 8: insoluble SC5215, Lane 9: negative control (Sigma C residues 1-326 without his tag, produced in *E. coli*). Lane 10: molecular weight marker. Arrow indicates sigma C protein.
Figure 1B:
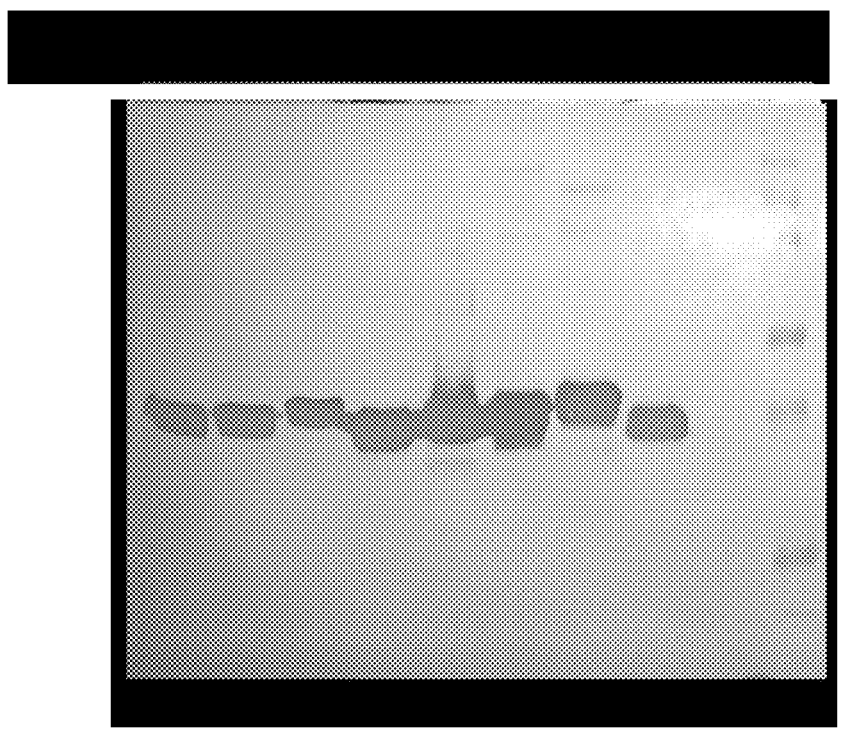

FIG. 1 shows the efficient expression of the 122-326 fragment of four different reo virus isolates: SC1133, SC528, SC5223 and SC5215.

Example 2

Antibody Response to Vaccination

Following vaccination, the immunogenicity of the SC proteins and the ability of the produced antibodies to detect the virus were tested by ELISA. Using SC122-326 as the antigen, antibodies derived following vaccination with proteins SC122-326 and SC192-326 detected the antigen at high titers of 1:800,000. The mean of the titers of birds in this group were significantly higher ($P<0.001$) than those in the negative control, whereas the mean of the antibody titer derived following vaccination with SC1-326 protein were similar to those of the negative control (FIG. 2).

Figure 3:
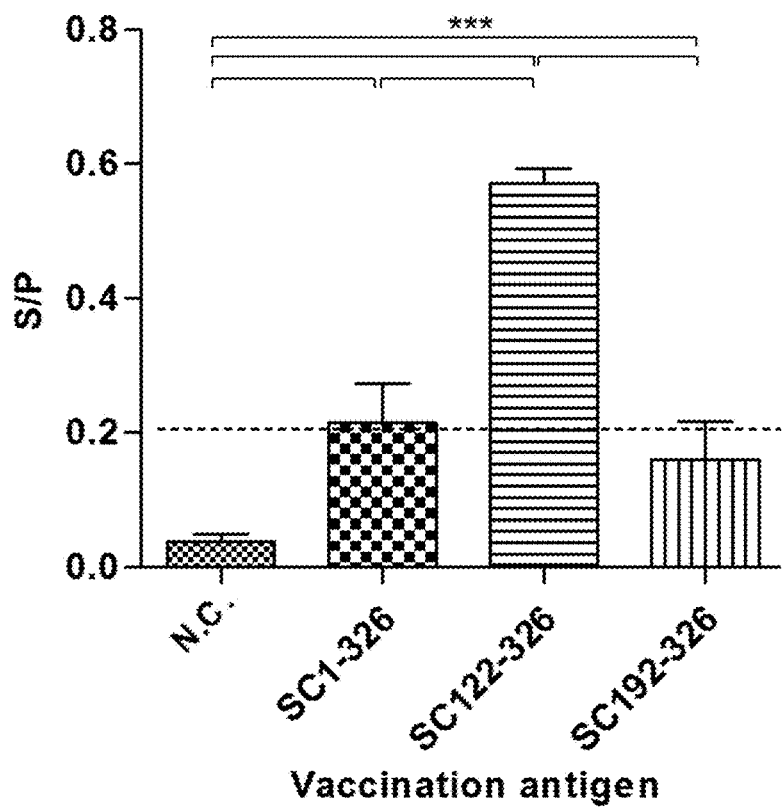
FIG. 3 depicts a bar graph showing virus detection by antibodies raised following protein injection. The relative level of anti-ARV antibody following injection with SC1-326, SC122-326 and SC192-326 is presented as the ratio between the ODs of the tested sample (S) and anti-ARV 1133 antibodies, provided in the KIT, that serve as positive control (P) (S/P). A value greater than 0.2 is considered positive (recognizing the virus). N.C—negative control (birds vaccinated with PBS in adjuvant). *** Significantly different at P<0.001.

Antibody level against whole virus following vaccination with SC192-326 or the negative control reached a value of 0.2 or lower, whereas antibodies derived following vaccination with SC1-326 or SC122-326 were positive (0.25 and 0.5, respectively) (FIG. 3). The S/P in SC122-326 group was significantly higher than in the other groups.

Similarly, following vaccination, the immunogenicity of the SC122-326 fragments of the four different RI Groups (SEQ ID NOs: 2, 3, 4 and 5) and the ability of the produced antibodies to detect the virus are tested by ELISA.

Example 3

Cell Proliferation

Splenocytes from the vaccinated chickens were examined for antigen-specific cell proliferation. Cells were treated with ConA as a control for proliferation of T cells, LPS as a control for proliferation of B cells (positive controls), PBS (negative control) and ARV (specific antigen). In the CTB assay, the measured absorbance was proportional to the number of viable cells. Results are presented as SI (mitogen- or antigen-stimulated/nonstimulated cells).

The positive control treatments exhibited proliferation following the stimulus. Cells stimulated with ARV showed significant differences among treatment groups. Cells from the group immunized with the virus or SC122-326 showed significant proliferation as compared to the negative control ($P<0.01$), whereas proliferation in group that were injected with SC1-326 was significantly lower than SC122-326 or the positive control groups ($P<0.05$) (FIG. 4).

Similarly, splenocytes from chickens vaccinated with a combination vaccine comprising polypeptides of SEQ ID NOs: 2, 3, 4 and 5 are examined for antigen-specific cell proliferation.

Example 4

Effect of SC122-326 in Priming the Response Against ARV

The effect of vaccination with SC122-326 as compared to vaccination with the whole-virus vaccine as an inducer of a primary response against ARV was tested. One group of chickens was injected with the ARV strain s1133 vaccine and the other with SC122-326. Two weeks later, ARV s1133 was injected into both groups. Primary vaccination with ARV or SC122-326, induce a similar significant elevation following secondary vaccination with whole ARV (FIG. 5).

Similarly, the effect of vaccination with a combination vaccine comprising polypeptides of SEQ ID NOs: 2, 3, 4 and 5 as compared to vaccination with the whole-virus vaccine as an inducer of a primary response against ARV is tested.

Example 5

Virus Neutralization

Sera from vaccinated birds were tested for neutralization ability against the virulent virus in SPF embryonated eggs. No protection was conferred by sera produced by the negative control birds or from the group injected with the SC1-326 (NI=0). In contrast, serum produced by birds injected with the protein SC122-326 conferred protection (neutralization capacity) similar to that achieved with antibodies that developed following vaccination with whole virus (NI>4) (Table 3).

Similarly, sera from birds vaccinated with a combination vaccine comprising polypeptides of SEQ ID NOs: 2, 3, 4 and 5 are tested for neutralization ability against the virulent virus in SPF embryonated eggs.

TABLE 5

Virus neutralization by antibodies against ARV or SC fragments.

| Vaccination | Neutralization index[a] |
|---|---|
| Adjuvant only (negative control) | 0 |
| ARV s1133 | 4 |
| SC1-326 | 0 |
| SC122-326 | >4 |

[a]Neutralization index (NI) value of 2 or higher is considered as neutralizing against that virus.

REFERENCES

Benavente, J. & Martinez-Costas, J., 2007. Avian reovirus: Structure and biology. *Virus Research*, 123(2), pp. 105-119. Available at: http://linkinghub.elsevier.com/retrieve/pii/S0168170206002772.

Fingerut, E. et al., 2003. A subunit vaccine against the adenovirus egg-drop syndrome using part of its fiber protein. *Vaccine*, 21, pp. 2761-2766.

Goldenberg, D. et al., 2011. Differentiating infected from vaccinated animals, and among virulent prototypes of reovirus. *Journal of Virological Methods*, 177(1), pp. 80-86. Available at: http://dx.doi.org/10.1016/j.jviromet.2011.06.023.

Goldenberg, D. et al., 2010. Genetic and antigenic characterization of sigma C protein from avian reovirus. *Avian pathology: journal of the W.V.P.A*, 39(3), pp. 189-199.

Grande, A. N. A. et al., 1997. Protein Architecture of Avian Reovirus S1133 and Identification of the Cell Attachment Protein. 71(1), pp. 59-64.

Guardado Calvo, P. et al., 2005. Structure of the Carboxy-terminal Receptor-binding Domain of Avian Reovirus Fibre SigmaC. *Journal of Molecular Biology*, 354(1), pp. 137-149. Available at: http://linkinghub.elsevier.com/retrieve/pii/S0022283605010995.

Guardado-Calvo, P. et al., 2009. Crystallographic structure of the α-helical triple coiled-coil domain of avian reovirus S1133 fibre. *Journal of General Virology*, 90(2009), pp. 672-677.

van der Heide, L., Kalbac, M. & Brustolon, M., 1983. Development of an attenuated apathogenic reovirus vaccine against viral arthritis/tenosynovitis. *Avian diseases*, 27(3), pp. 698-706. Available at: http://www.ncbi.nlm.nih.gov/pubmed/6314976 [Accessed Dec. 9, 2015].

Jones, R. C., 2000. Avian reovirus infections. *Revue scientifique et technique (International Office of Epizootics)*, 19(2), pp. 614-25. Available at: http://www.ncbi.nlm.nih.gov/pubmed/10935283 [Accessed Dec. 9, 2015].

Jung, K. M. et al., 2014. Use of IgY antibody to recombinant avian reovirus σC protein in the virus diagnostics. *Acta virologica*, 58(2), pp. 108-13. Available at: http://www.ncbi.nlm.nih.gov/pubmed/24957714 [Accessed Dec. 9, 2015].

Kant, A. et al., 2003. Classification of Dutch and German avian reoviruses by sequencing the sigma C protein. *Veterinary research*, 34(2), pp. 203-12. Available at: http://www.ncbi.nlm.nih.gov/pubmed/12657212 [Accessed Dec. 9, 2015].

Lu, H. et al., 2015. Isolation and molecular characterization of newly emerging avian reovirus variants and novel strains in Pennsylvania, USA, 2011-2014. *Scientific Reports*, 5 (April), p. 14727. Available at: http://www.nature.com/articles/srep14727.

Lublin, A. et al., 2011. Wide-range protection against avian reovirus conferred by vaccination with representatives of four defined genotypes. *Vaccine*, 29(47), pp. 8683-8688. Available at: http://dx.doi.org/10.1016/j.vaccine.2011.08.114.

McAleer, W. J. et al., 1984. Human hepatitis B vaccine from recombinant yeast. *Nature*, 307(5947), pp. 178-80. Available at: http://www.ncbi.nlm.nih.gov/pubmed/6318124 [Accessed Dec. 9, 2015].

Pitcovski, J. et al., 2005. A subunit vaccine against hemorrhagic enteritis adenovirus. *Vaccine*, 23, pp. 4697-4702.

Pitcovski, J. et al., 2003. Development and large-scale use of recombinant VP2 vaccine for the prevention of infectious bursal disease of chickens. *Vaccine*, 21, pp. 4736-4743.

Shapouri, M. R. et al., 1995. Cloning, sequencing and expression of the S1 gene of avian reovirus. *The Journal of general virology*, 76 (Pt 6)(1995), pp. 1515-20. Available at: http://www.ncbi.nlm.nih.gov/pubmed/7782781.

Shapouri, M. R. S. et al., 1996. Characterization of monoclonal antibodies against avian reovirus strain S1133. *Avian pathology: journal of the W.V.P.A*, 25(1), pp. 57-67. Available at: http://www.ncbi.nlm.nih.gov/pubmed/18645837 [Accessed Dec. 9, 2015].

Troxler, S. et al., 2013. Identification of a new reovirus causing substantial losses in broiler production in France, despite routine vaccination of breeders. *The Veterinary record*, 172(21), p. 556. Available at: http://www.ncbi.nlm.nih.gov/pubmed/23636701 [Accessed Dec. 9, 2015].

Valentino, K. & Poronsky, C. B., 2015. Human Papillomavirus Infection and Vaccination. *Journal of pediatric nursing*. Available at: http://www.sciencedirect.com/science/article/pii/S0882596315003267 [Accessed Nov. 22, 2015].

Vasserman, Y. et al., 2004. The influence of reovirus sigma C protein diversity on vaccination efficiency. *Avian diseases*, 48(2), pp. 271-8. Available at: http://www.ncbi.nlm.nih.gov/pubmed/15283414 [Accessed Dec. 9, 2015].

Wu, H. et al., 2005. Yeast-derived sigma C protein-induced immunity against avian reovirus. *Avian diseases*, 49(2), pp. 281-4. Available at: http://www.ncbi.nlm.nih.gov/pubmed/16094835 [Accessed Dec. 9, 2015].

The invention claimed is:

1. A vaccine comprising an adjuvant and an at least one isolated polypeptide, said at least one isolated polypeptide comprising an amino acid sequence corresponding to the amino acid residues forming a full or partial a-helical domain, a hinge domain, a β-triple spiral domain, and a full or partial globular head domain, of an avian reovirus sigma C protein, and said amino acid sequence, lacking the amino acid sequence that is N-terminal to said a-helical domain.

2. The vaccine of claim 1, wherein said adjuvant is selected from the group consisting of heat-labile enterotoxin (LT), complete Freund adjuvant, incomplete Freund adjuvant, and aluminium hydroxide.

3. A viral vector comprising a control element operably linked to a nucleic acid molecule comprising a nucleic acid sequence encoding at least one isolated polypeptide comprising an amino acid sequence corresponding to the amino acid residues forming a full or partial a-helical domain, a hinge domain, a β-triple spiral domain and a full or partial globular head domain, of an avian reovirus sigma C protein, and said amino acid sequence, lacking the amino acid sequence that is N-terminal to said a-helical domain.

4. The vaccine of claim 1, wherein said at least one isolated polypeptide is at least two different polypeptides, each one of said at least two different polypeptides being derived from a representative sigma C protein of one of two, three or four groups of different sigma C proteins, wherein the defining feature of each group is that the amino acid sequences of the different sigma C proteins of said group have at least 75% identity.

5. The vaccine of claim 4, wherein said at least one isolated polypeptide is four different isolated polypeptides, wherein the first of said four different polypeptides is derived from a sigma C protein that has at least 75% identity to SEQ ID NOs: 6-11 (Group I); the second of said four different polypeptides is derived from a sigma C protein that has at least 75% identity to SEQ ID NOs: 12-16 (Group II); the third of said four different polypeptides is derived from a sigma C protein that has at least 75% identity to SEQ ID NOs: 17-22 (Group III); and the fourth of said four different polypeptides is derived from a sigma C protein that has at least 75% identity to SEQ ID NOs: 1 and 23 (Group IV).

6. The vaccine of claim 5, wherein the first of said four different polypeptides is derived from a sigma C protein that has at least 80%, at least 85%, at least 90%, or at least 95, 96, 97, 98, or 99% identity to SEQ ID NO: 8; the second of said four different polypeptides is derived from a sigma C protein that has at least 80%, at least 85%, at least 90%, or at least 95, 96, 97, 98, or 99% identity to SEQ ID NO: 16; the third of said four different polypeptides is derived from a sigma C protein that has at least 80%, at least 85%, at least 90%, or at least 95, 96, 97, 98, or 99% identity to SEQ ID NO: 19; and the fourth of said four different polypeptides is derived from a sigma C protein that has at least 80%, at least 85%, at least 90%, or at least 95, 96, 97, 98, or 99% identity to SEQ ID NO: 23.

7. The vaccine of claim 5, wherein the first of said four different polypeptides is derived from a polypeptide selected from the group consisting of SEQ ID NO: 6-11 (Group I); the second of said four different polypeptides is derived from a polypeptide selected from the group consisting of SEQ ID NO: 12-16 (Group II); the third of said four different polypeptides is derived from a polypeptide selected from the group consisting of SEQ ID NO: 17-22 (Group III); and the fourth of said four different polypeptides is derived from a polypeptide selected from the group consisting of SEQ ID NO: 1 and 23 (Group IV).

8. The vaccine of claim 7, wherein said four different polypeptides have amino acid sequences as set forth in SEQ ID NO: 2, SEQ ID NO: 3, SEQ ID NO: 4 and SEQ ID NO: 5.

9. A method for vaccination of an avian species against avian reovirus or for inducing an avian immune response conferring protection against avian reovirus, which comprises administering a vaccine of claim 1 to a bird.

10. The method of claim 9, which induces the production of higher systemic levels of neutralizing anti-sigma C protein antibody as compared with the systemic levels of said antibody obtained after administration to said bird of full length sigma C protein of the ARV strain s1133.

11. The method of claim 9, comprising administering said vaccine to birds by injection, intradermally or subcutaneously; or orally via the drinking water.

12. The vaccine of claim 1, wherein the at least one isolated polypeptide comprises an internal amino acid sequence corresponding to amino acid residues 70-326, 117-326 or 122-326 of the sigma C protein of the ARV strain S1133 as set forth in SEQ ID NO: 1.

13. The vaccine of claim 1, wherein the internal amino acid sequence has at least 40%, at least 50%, at least 60%, at least 70%, at least 80%, at least 85%, at least 90%, or at least 95, 96, 97, 98, or 99% identity to the internal amino acid sequence of a sigma C protein selected from the group consisting of isolate S1133 (SEQ ID NO:1), isolate ISR521 (SEQ ID NO:6), isolate ISR526 (SEQ ID NO:7), isolate ISR5215 (SEQ ID NO:8), isolate ISR5220 (SEQ ID NO:9), isolate ISR5225 (SEQ ID NO:10), isolate ISR5226 (SEQ ID NO:11), isolate ISR522 (SEQ ID NO:12), isolate ISR5217 (SEQ ID NO:13), isolate ISR5221 (SEQ ID NO:14), isolate ISR5222 (SEQ ID NO:15), isolate ISR5223 (SEQ ID NO:16), isolate ISR524 (SEQ ID NO:17), isolate ISR527 (SEQ ID NO:18), isolate ISR528 (SEQ ID NO:19), isolate ISR529 (SEQ ID NO:20), isolate ISR5211 (SEQ ID NO:21), isolate ISR5213 (SEQ ID NO:22), isolate 59103 (SEQ ID NO:23), isolate ISR5212 (SEQ ID NO:24), isolate ISR5210 (SEQ ID NO:25), isolate ISR5216 (SEQ ID NO:26), isolate ISR5234 (SEQ ID NO:27), isolate ISR5231 (SEQ ID NO:28), isolate ISR5229 (SEQ ID NO:29), isolate ISR525 (SEQ ID NO:30), isolate ISR523 (SEQ ID NO:31), isolate ISR5224 (SEQ ID NO:32), isolate ISR5219 (SEQ ID NO:33), and isolate ISR5233 (SEQ ID NO:34).

14. The vaccine of claim 13, wherein the internal amino acid sequence is within the internal amino acid sequence of a sigma C protein selected from the group consisting of isolate S1133 (SEQ ID NO:1), isolate ISR521 (SEQ ID NO:6), isolate ISR526 (SEQ ID NO:7), isolate ISR52151 (SEQ ID NO:8), isolate SR5220 (SEQ ID NO:9), isolate ISR5225 (SEQ ID NO:10), isolate ISR5226 (SEQ ID NO:11), isolate ISR522 (SEQ ID NO:12), isolate ISR5217 (SEQ ID NO:13), isolate ISR5221 (SEQ ID NO:14), isolate ISR5222 (SEQ ID NO:15), isolate ISR5223 (SEQ ID NO:16), isolate ISR524 (SEQ ID NO:17), isolate ISR527 (SEQ ID NO:18), isolate ISR528 (SEQ ID NO:19), isolate ISR529 (SEQ ID NO:20), isolate ISR5211 (SEQ ID NO:21), isolate ISR5213 (SEQ ID NO:22), and isolate 59103 (SEQ ID NO:23).

15. The vaccine of claim 14, wherein the at least one isolated polypeptide comprises an amino acid sequence selected from SEQ ID NO: 2, SEQ ID NO: 3, SEQ ID NO: 4 and SEQ ID NO: 5.

16. The viral vector of claim 3, wherein said nucleic acid molecule encodes at least two different polypeptides; each one of said at least two different polypeptides is derived from a representative of one of two, three or four groups of different sigma C proteins, wherein the defining feature of each group is that the amino acid sequences of the different sigma C proteins of said group has at least 75% identity.

17. The viral vector of claim 16, wherein said at least one isolated polypeptide is four different isolated polypeptides, wherein the first of said four different polypeptides is derived from a sigma C protein that has at least 75% identity to SEQ ID NOs: 6-11 (Group I); the second of said four different polypeptides is derived from a sigma C protein that has at least 75% identity to SEQ ID NOs: 12-16 (Group II); the third of said four different polypeptides is derived from a sigma C protein that has at least 75% identity to SEQ ID NOs: 17-22 (Group III); and the fourth of said four different polypeptides is derived from a sigma C protein that has at least 75% identity to SEQ ID NOs: 1 and 23 (Group IV).

18. The viral vector of claim 17, wherein the first of said four different polypeptides is derived from a sigma C protein that has at least 80%, at least 85%, at least 90%, or at least 95, 96, 97, 98, or 99% identity to SEQ ID NO: 8; the second of said four different polypeptides is derived from a sigma C protein that has at least 80%, at least 85%, at least 90%, or at least 95, 96, 97, 98, or 99% identity to SEQ ID NO: 16; the third of said four different polypeptides is derived from a sigma C protein that has at least 80%, at least 85%, at least 90%, or at least 95, 96, 97, 98, or 99% identity to SEQ ID NO: 19; and the fourth of said four different polypeptides is derived from a sigma C protein that has at least 80%, at least 85%, at least 90%, or at least 95, 96, 97, 98, or 99% identity to SEQ ID NO: 23.

19. The viral vector of claim 17, wherein the first of said four different polypeptides is derived from a polypeptide selected from the group consisting of SEQ ID NO: 6-11 (Group I); the second of said four different polypeptides is derived from a polypeptide selected from the group consisting of SEQ ID NO: 12-16 (Group II); the third of said four different polypeptides is derived from a polypeptide selected from the group consisting of SEQ ID NO: 17-22 (Group III); and the fourth of said four different polypeptides is derived from a polypeptide selected from the group consisting of SEQ ID NO: 1 and 23 (Group IV).

20. The viral vector of claim 18, wherein said four different polypeptides have amino acid sequences as set forth in SEQ ID NO: 2, SEQ ID NO: 3, SEQ ID NO: 4 and SEQ ID NO: 5.

21. The vaccine of claim 1, further comprising a preservative selected from the group consisting of thimerosal and 20% water-in-oil emulsion.

22. The vaccine of claim 1, which induces a protective immune response against an infectious avian reovirus.

23. The vaccine of claim 1, which induces the production of higher systemic levels of neutralizing anti-sigma C protein antibody as compared with the systemic levels of said antibody obtained after administration to a bird of full length sigma C protein of SEQ ID NO: 1.

* * * * *